(12) United States Patent
Weinshenker et al.

(10) Patent No.: US 7,232,805 B2
(45) Date of Patent: Jun. 19, 2007

(54) COBALAMIN CONJUGATES FOR ANTI-TUMOR THERAPY

(75) Inventors: Ned M. Weinshenker, Salt Lake City, UT (US); Frederick G. West, Edmonton (CA); Barbara A. Araneo, Salt Lake City, UT (US); Weiping Li, Salt Lake City, UT (US)

(73) Assignee: Inflabloc Pharmaceuticals, Inc., Salt Lake City, UT (US)

( * ) Notice: Subject to any disclaimer, the term of this patent is extended or adjusted under 35 U.S.C. 154(b) by 93 days.

(21) Appl. No.: 10/659,501

(22) Filed: Sep. 10, 2003

(65) Prior Publication Data

US 2005/0054607 A1  Mar. 10, 2005

(51) Int. Cl.
*A01N 43/04* (2006.01)
*A61K 31/70* (2006.01)
*C07G 3/00* (2006.01)
*C07G 11/00* (2006.01)
*C07H 15/00* (2006.01)
*C07H 17/00* (2006.01)

(52) U.S. Cl. .................. 514/33; 514/2; 514/6; 514/25; 514/35; 514/43; 514/52

(58) Field of Classification Search .......... 514/2, 514/6, 25, 33, 35, 43, 52
See application file for complete search history.

(56) References Cited

U.S. PATENT DOCUMENTS

| | | | |
|---|---|---|---|
| 3,130,189 A | 4/1964 | Hannus | 260/112 |
| 5,405,839 A | 4/1995 | Toraya | 514/52 |
| 5,428,023 A | 6/1995 | Russell-Jones | 514/21 |
| 5,449,720 A | 9/1995 | Russell-Jones | 525/54.1 |
| 5,548,064 A | 8/1996 | Russell-Jones | 530/380 |
| 5,574,018 A | 11/1996 | Habberfield | 514/21 |
| 5,589,463 A | 12/1996 | Russell-Jones | 514/21 |
| 5,739,287 A | 4/1998 | Wilbur | 530/367 |
| 5,807,832 A | 9/1998 | Russell-Jones | 514/21 |
| 5,840,712 A | 11/1998 | Morgan | 514/52 |
| 5,840,880 A | 11/1998 | Morgan | 536/26.4 |
| 5,863,900 A | 1/1999 | Russell-Jones | 514/15 |
| 5,869,465 A | 2/1999 | Morgan | 514/52 |
| 5,869,466 A | 2/1999 | Russell-Jones | 514/52 |
| 6,083,926 A | 7/2000 | Morgan, Jr. | 514/52 |
| 6,150,341 A | 11/2000 | Russell-Jones | 514/52 |
| 6,214,345 B1 | 4/2001 | Firestone | 424/178.1 |
| 6,262,253 B1 | 7/2001 | Russell-Jones | 536/26.41 |
| 6,315,978 B1 | 11/2001 | Grissom | 424/1.53 |
| 6,797,521 B2 * | 9/2004 | Grissom et al. | 436/505 |
| 2002/0042394 A1 | 4/2002 | Hogenkamp | 514/53 |
| 2002/0049154 A1 | 4/2002 | Grissom | 514/6 |
| 2002/0049155 A1 | 4/2002 | Hogenkamp | 514/7 |
| 2002/0111294 A1 | 8/2002 | Grissom | 514/6 |
| 2002/0115595 A1 | 8/2002 | Grissom | 514/6 |
| 2002/0151525 A1 | 10/2002 | Collins | 514/80 |
| 2002/0192683 A1 | 12/2002 | Grissom | 435/6 |

FOREIGN PATENT DOCUMENTS

| | | |
|---|---|---|
| EP | 0220030 B1 | 4/1987 |
| GB | 944428 B1 | 12/1963 |
| WO | WO 98/08859 A1 | 3/1998 |
| WO | WO 98/13059 A | 4/1998 |
| WO | WO 99/65930 A1 | 12/1999 |
| WO | WO 00/33810 A1 | 6/2000 |
| WO | WO 00/56404 A1 | 9/2000 |
| WO | WO 00/62808 A2 | 10/2000 |
| WO | WO 01/28592 A1 | 4/2001 |
| WO | WO 01/28595 A1 | 4/2001 |
| WO | WO 97/14711 A1 | 4/2001 |
| WO | WO 01/30967 A1 | 5/2001 |

(Continued)

OTHER PUBLICATIONS

Dubowchik et al. Bioorganic & Medicinal Chemistry Letters (1998), vol. 8, pp. 3341-3346.*

(Continued)

*Primary Examiner*—Patrick T. Lewis
(74) *Attorney, Agent, or Firm*—Thorpe North & Western LLP

(57) ABSTRACT

The present invention provides a cobalamin-drug conjugate suitable for the treatment of tumor related diseases. Cobalamin is indirectly covalently bound to an anti-tumor drug via a cleavable linker and one or more optional spacers. Cobalamin is covalently bound to a first spacer or the cleavable linker via the 5'-OH of the cobalamin ribose ring. The drug is bound to a second spacer of the cleavable linker via an existing or added functional group on the drug. After administration, the conjugate forms a complex with transcobalamin (any of its isoforms). The complex then binds to a receptor on a cell membrane and is taken up into the cell. Once in the cell, an intracellular enzyme cleaves the conjugate thereby releasing the drug. Depending upon the structure of the conjugate, a particular class or type of intracellular enzyme affects the cleavage. Due to the high demand for cobalamin in growing cells, tumor cells typically take up a higher percentage of the conjugate than do normal non-growing cells. The conjugate of the invention advantageously provides a reduced systemic toxicity and enhanced efficacy as compared to a corresponding free drug.

21 Claims, 18 Drawing Sheets

FOREIGN PATENT DOCUMENTS

| WO | WO 02/055530 A2 | 7/2002 |
| WO | WO 02/074171 A1 | 9/2002 |
| WO | WO 03/025139 A1 | 3/2003 |
| WO | WO 03/026674 A1 | 4/2003 |
| WO | WO 2004/041828 A | 5/2004 |

OTHER PUBLICATIONS

Dubowchik et al. Bioorganic & Medicinal Chemistry Letters (1998), vol. 8, pp. 3347-3352.*

P.L. Carl et al.; "A novel connector linkage applicable in prodrug design"; J. Med. Chem. (1981), 24(5), pp. 479-480.

B.E. Toki et al.; "Protease-mediated fragmentation of p-amidobenzyl ethers: A new strategy for the activation of anticancer drugs"; J. Org. Chem. (2002), 67(6), pp. 1866-1872.

Dubowchik et al., Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity, Bioconjugate Chem., Jun. 18, 2002, pp. 855-869, vol. 13.

* cited by examiner

Cathepsin B-cleavable B12-Dox conjugate

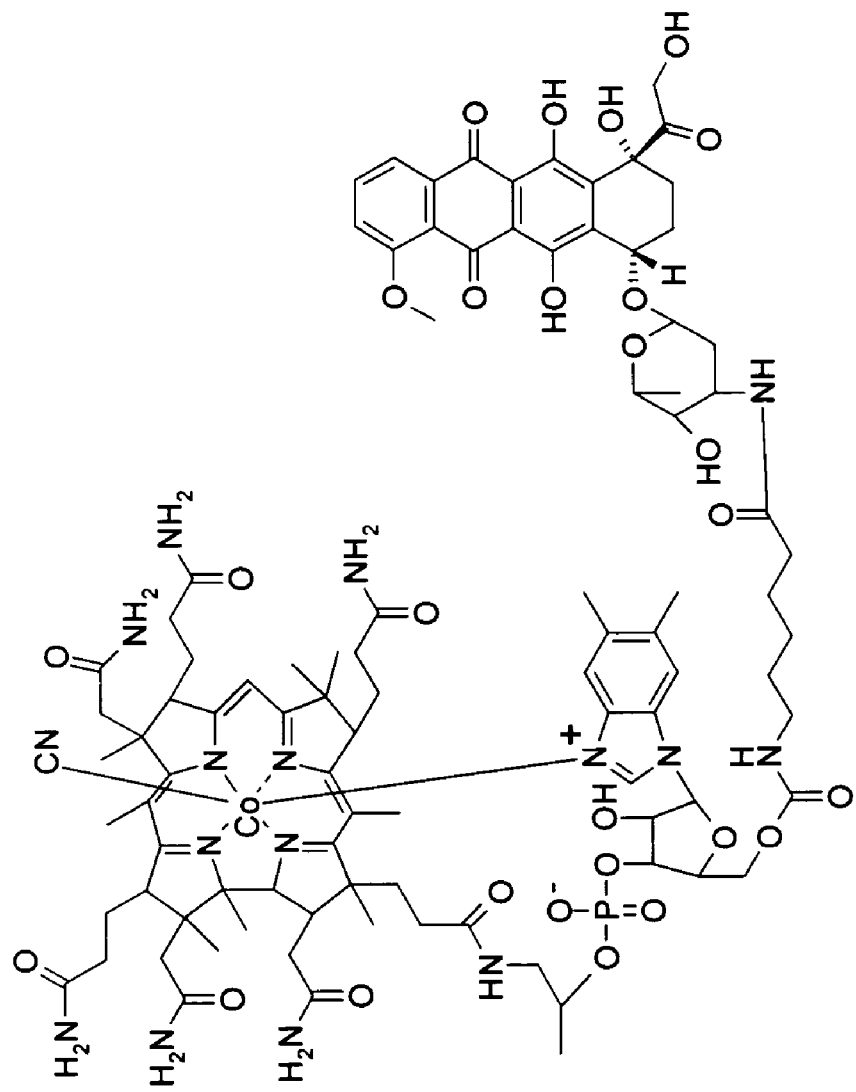
FIG. 1b  Stable B12-Dox conjugate

COBALAMIN CONJUGATES FOR ANTI-TUMOR THERAPY

FIELD OF THE INVENTION

This invention pertains to a conjugate of cobalamin, to a method of its use and to a method of its preparation. More particularly, it pertains to a cobalamin conjugate for the treatment of tumor (cancer) related diseases.

BACKGROUND OF THE INVENTION

Antiproliferation drugs, e.g. anti-tumor or anticancer drugs, and their analogues, derivatives and prodrugs are well known for use in the treatment of cancer, tumor and other cellular proliferation related diseases. Methods for their administration are varied and have met with a range of successes and failures. Goals in the development of antiproliferative agent-containing pharmaceutical compositions and formulations include improving targeted delivery of these drugs in order to minimize systemic toxicity to subjects being treated with these drugs, maintaining efficacy of these drugs upon derivatization thereof. There have been some successes in improving targeted delivery of the drugs to cancer or tumor cells, and maintaining the efficacy of the drugs even after derivatization thereof. Even so, targeted delivery combined with high efficacy remains a key goal in anti-tumor therapy.

Derivatization of drugs with naturally occurring biologically active components has been evaluated as a means for improving targeted delivery of these drugs. To that end, cobalamin conjugates comprising drugs, proteins, nucleic acids, amino acids, peptides, hormones or other components have been developed in an effort to improve bioavailability by exploiting the biological mechanism of cobalamin cellular uptake. In principle, a bioconjugate (CBD) comprising an agent covalently linked to cobalamin (CB) becomes bound to a protein in vivo. Depending upon the site of administration, the protein is Intrinsic Factor (IF) or transcobalamin (TCCB) I, II or III. IF is a naturally occurring protein in the gastrointestinal tract that binds to CB. After oral administration of a cobalamin bioconjugate, it is bound to IF to form a complex (IF-CBD) that is actively transported across the lumen of the GI tract. Once in the plasma, IF dissociates from the IF-CBD complex thereby releasing CBD into the plasma compartment. TCCB is responsible for cellular uptake of CB across the cellular membrane. TCCB binds to CBD in the plasma to form a complex TCCB-CBD. The TCCB-CBD complex is then actively transported across the cellular membrane via the TCCB receptors on the cell membrane. After entry into the cell, TCCB undergoes intracellular dissociation from the TCCB-CBD complex thereby releasing CBD intracellularly. A number of publications report the preparation of cobalamin conjugates for the above-mentioned uses.

U.S. Pat. Nos. 5,739,313; 6,004,533; 6,096,290; 6,211,355; and PCT Publication WO 97/18231 disclose radionuclide labeling of vitamin B12 through the propionamide moieties on naturally occurring vitamin B12. The propionamide moieties at the b-, d-, and e-positions of the corrin ring were converted to monocarboxylic acids, through a mild hydrolysis, and the carboxylic acids were separated by column chromatography. A bifunctional linking moiety was then attached to the carboxylate function through an amide linkage, and a chelating agent was attached to the linking moiety again through an amide linkage. The chelating moiety was used to attach a radionuclide to the vitamin so that it could be used for therapeutic or diagnostic purposes.

Hogenkamp et al. in WO 01/28595 (PCT/USOO/10098) disclose a series of cobalamin conjugates that are linked via a protein linker to a detectable group, which is useful in the imaging of tumors. The linker is not attached to cobalamin via the 5'-OH group. Hogenkamp et al. suggest that such compounds may be useful in the treatment of tumors.

Hogenkamp et al. in WO 01/28592 (PCT/USOO/10097) disclose a series of cobalamin conjugates that are linked directly to or indirectly by a linker to a residue of a chemotherapeutic agent, which is useful in the treatment of abnormal cellular proliferation. The linker is not attached to cobalamin via the 5'-OH group. A doxorubicin conjugate is contemplated and a proposed synthesis therefor is included in the application. No actual exemplification of compounds is included in the application even though a wide range of antiproliferative agents are disclosed as being suitable. The conjugation is proposed to occur through a carboxylic acid moiety of the cobalamin.

Collins et al. in WO 00/62808 (PCT/USOO/10100) disclose a series of cobalamin conjugates that are linked directly or by a linker to a residue of a molecule comprising B-10 or Gd-157, which are useful in the treatment of abnormal cellular proliferation. A neutron capture therapy target is linked to cobalamin. After systemic administration, the conjugate is absorbed into a tumor cell. Then neutron capture irradiation is administered. Proposed linkage sites include the amide sites and the cobalt. The 5'-OH of the cobalamin ribose ring is not proposed.

PCT Publication WO 98/08859 to Grissom et al. discloses conjugates containing a bioactive agent and an organocobalt complex in which the bioactive agent is covalently bound directly or indirectly, via a spacer, to the cobalt atom. The bioactive agent can be a chemotherapeutic agent (anti-tumor drug). The bioactive agent is released from the bioconjugate by the cleavage of the weak covalent bond between the bioactive agent and the cobalt atom as a result of normal displacement by cellular nucleophiles or enzymatic action, or by application of an external signal (e.g., light, photoexcitation, ultrasound, or the presence of a magnetic field). The conjugates are reportedly targeted for site specific release of bioactive agents in cells, tissues, or organs.

PCT International Publication WO 03/025139 to Collins et al. discloses a conjugate for the delivery of nucleic acids via coupling to VB12, cobalamin. A degradable linker is used. Proposed linkage is through any of the amide sites or the 5'-OH site. Antisense sequences, nonsense sequences, antisense mimics, nucleic acids and nucleic acid analogues are contemplated.

U.S. Pat. No. 5,428,023 to Russell-Jones et al. discloses a vitamin B12 conjugate for delivering oral hormone formulations. Russell-Jones teaches that the vitamin B12 conjugate must be capable of binding in vivo to intrinsic factor, enabling uptake and transport of the complex from the intestinal lumen of a vertebrate host to the systemic circulation of the host. The hormones are attached to the vitamin B12 through a hydrolyzed propionamide linkage on the vitamin. The patent states that the method is useful for orally administering hormones, bioactive peptides, therapeutic agents, antigens, and haptens, and lists as therapeutic agents neomycin, salbutamol cloridine, pyrimethamine, penicillin G, methicillin, carbenicillin, pethidine, xylazine, ketamine hydrochloride, mephanesin and iron dextran.

U.S. Pat. No. 5,548,064 and No. 6,262,253 to Russell-Jones et al. disclose a vitamin B12 conjugate for delivering erythropoietin and granulocyte colony stimulating factor, using the same approach as the '023 patent.

PCT Publication WO 94/27641 to Russell-Jones et al discloses vitamin B12 linked through a polymer to various active agents wherein the conjugate is capable of binding to intrinsic factor for systemic delivery. In particular, the document discloses the attachment of various polymeric linkers to the propionamide positions of the vitamin B12 molecule, and the attachment of various bioactive agents to the polymeric linker. Exemplary bioactive agents include hormones, bioactive peptides and polypeptides, anti-tumor agents, antibiotics, antipyretics, analgesics, anti-inflammatory agents, and haemostatic agents. Exemplary polymers include carbohydrates and branched chain amino acid polymers. The linkers used in WO 94/27641 are polymeric (each having a molecular weight of about 5000 or greater). The linkers are described as exhibiting a mixture of molecular weights, due to the polymerization process by which they are made.

PCT Publication WO 99/65930 and U.S. Pat. No. 6,150,341 to Russell-Jones et al. disclose the attachment of various agents to the 5'-OH position on the vitamin B12 (VB12) ribose ring. The publications indicate that the system can be used to attach polymers, nanoparticles, therapeutic agents, proteins, and peptides to the vitamin. Russell-Jones et al. disclose the preparation of 5'-OH VB12 derivatives via the use of an active carbonyl electrophile. After reacting the VB12 5'-OH with the carbonyl electrophile, a linker, diamino spacer, or other molecule is reacted with activated 5'-OH site. Alternatively, the 5'-OH site is converted to an ester site that is then derivatized. Linking of the VB12 derivatives to drugs is contemplated.

PCT International Publication WO 02/074171 (PCT/US02/08285) and U.S. Pregrant Patent Publication 2002/0192683 to Grissom et al. disclose fluorescent cobalamin derivatives. A fluorescent moiety is linked to the cobalamin preferably via the corrin ring or the 5'-OH group. The compounds are used to detect cancer cells, identify cells that are potentially susceptible to anticancer therapy and other such methods. It does not disclose an anticancer drug attached to the 5'-OH group.

U.S. Pat. No. 5,574,018 to Habberfield et al. discloses conjugates of vitamin B12 in which a therapeutically useful protein is attached to the primary hydroxyl site of the ribose moiety. The patent lists erythropoietin, granulocyte-colony stimulating factor and human intrinsic factor as therapeutically useful proteins, and indicates that the conjugates are particularly well adapted for oral administration.

U.S. Pat. No. 5,840,880 to Morgan, Jr. et al. discloses vitamin B12 conjugates to which are linked receptor modulating agents, which affect receptor trafficking pathways that govern the cellular uptake and metabolism of vitamin B12. The receptor modulating agents are linked to the vitamin at the b-, d-, or e-position.

U.S. Pregrant Patent Publication 2002/0151525 to Collins et al. discloses a range of conjugates of VB-12 linked to an antiproliferative drug. The drug can be linked by a variety of different linkers at a number of different sites on the VB-12 molecule including the 5'-OH site. Doxorubicin is included among a laundry list of suitable antiproliferative drugs. Although a prophetic and general description for synthesis of a conjugate comprising doxorubicin attached to a carboxylic acid moiety of VB-12 is disclosed, there is no actual exemplification of such compound. There is also no other synthetic procedure disclosed for any other specific conjugates, especially conjugates of the 5'-OH site.

U.S. Pregrant Patent Publications No. 2002/0115595 and No. 2002/0049154 to Grissom et al. discloses organocobalt derivatives of VB12. The derivatives are disclosed as being suitable for oral and i.v. administration. Several anti-tumor drugs, such as doxorubicin, methotrexate, and carboplatin, are disclosed as being suitable for conjugation. Cleavage of the anti-tumor drug from a self-destructing linker is proposed to occur by cellular nucleophiles, enzymes, light or sound. Grissom et al. propose a method of treating cancer with the conjugate.

U.S. Pat. No. 6,315,978 to Grissom et al. discloses organocobalt derivatives of VB-12 adapted to oral or i.v. administration. Anti-tumor drugs that can be conjugated to the VB-12 include doxorubicin, methotrexate, and carboplatin. They suggest cleavage of the anti-tumor drug from the linker by cellular nucleophiles or enzymes or light or sound. The linker is a self-destructing linker that breaks away from the drug after it has been removed from the VB-12. They also suggest a method of treating cancer with the conjugate.

U.S. Pregrant Patent Publication 2002/0042394 to Hogenkamp et al. discloses VB-12 conjugated with an antibiotic optionally for use as an imaging agent. Hogenkamp identify topical antineoplasts (EFUDEX: fluorouracil; fluoroplex) as antibiotic compounds suitable for use in the conjugate. They suggest antibiotic compounds attached to VB-12 at a variety of sites including the 5'-OH. They do not disclose intravenous administrable anti-tumor conjugates.

U.S. Pat. No. 5,449,720 to Russell-Jones et al. discloses the use of polymer as a linker between VB-12 and an active agent. The conjugate is defined as $(V-Q)_n-P-(Q'-A)_m$ where V is VB-12; P is an optionally biodegradable polymer; A is an active agent; and Q, Q' are optional spacers or cross-linking agents. Russell-Jones et al. disclose a list of potential anti-tumor agents and many other drugs that can be conjugated to the VB-12 via carboxyl moieties. However, they do not disclose 5'-OH derivatives of VB-12.

U.S. Pat. No. 5,589,463 to Russell Jones discloses utilization of the VB-12 uptake mechanism for transport of VB-12 derivatives across the lumen of the GI tract following oral administration. The VB-12 derivative linked to an active agent. A range of active agents but not anti-tumor compounds is disclosed. A cross-linking agent is used to form the linker. Antibiotics attached to VB-12 are disclosed to enhance uptake of drug. They also do not disclose 5'-OH derivatives of VB-12.

U.S. Pat. No. 5,739,287 to Wilbur et al., No. 5,840,712 to Morgan Jr. et al., No. 5,840,880 to Morgan Jr. et al., No. 5,869,465 to Morgan Jr. et al. and No. 6,083,926 to Morgan Jr. et al. disclose biotinylated VB-12 discloses designed to block VB-12 receptors. Their 5'-OH derivatives are prepared according to procedure of Toraya (*Bioinorg. Chem.* (1975), 4, 245-255). They disclose variety of different groups that can be used to attach the linker to the VB-12. For the treatment of cancer, they disclose coadministration of methotrexate, or another anticancer or anti-tumor drug, along with a modified VB-12 thereby employing two different mechanisms: depletion of VB-12 in growing cancer cells coupled with administration of a chemotherapeutic agent. They do not suggest conjugation of the methotrexate with the VB-12.

U.S. Pat. No. 5,807,832 to Russell-Jones et al discloses the use of a cross-linking agent to conjugate VB-12 and a bioactive molecule (hormone, antibiotic, hapten, antigen, protein, secretory product). They do not disclose intracellular enzyme cleavage of the conjugate, nor do they disclose anti-tumor drugs or 5'-OH derivatives of VB-12.

U.S. Pat. No. 5,863,900 to Russell-Jones et al. discloses LHRH antagonists (ANTIDE-1, ANTIDE-2, ANTIDE-3) linked to VB-12 via carboxylate linkage with a diamine or dithiol linkage. ANTIDE components resist enzymatic hydrolysis in the GI tract. They suggest cleavage of ANTIDE from VB-12 in vivo. They suggest the use of analogues for in vivo cleavage by transglutaminase, but did not succeed in doing so. They also do not disclose anti-tumor compounds as conjugates of VB-12.

U.S. Pat. No. 6,214,345 to Firestone et al. discloses the preparation and use of conjugates of an anti-tumor drug and a targeting ligand (antibody or protein) linked by way of a self-destructing (self-immolative spacer). VB-12 is not disclosed as a suitable ligand. Instead, macromolecules such as antibodies and the like are disclosed as suitable ligands. Doxorubicin is claimed as a drug that can be included in the conjugate.

Other patent describing the use of Vitamin B12 include U.S. Pat. No. 3,936,440 to Nath (Method of Labeling Complex Metal Chelates with Radioactive Metal Isotopes); U.S. Pat. No. 4,209,614 to Bernstein et al., (Vitamin B12 Derivatives Suitable for Radiolabeling); U.S. Pat. No. 4,279,859 (Simultaneous Radioassay of Folate and Vitamin B12); U.S. Pat. No. 4,283,342 to Yollees (Anticancer Agents and Methods of Manufacture); U.S. Pat. No. 4,301,140 to Frank et al (Radiopharmaceutical Method for Monitoring Kidneys); U.S. Pat. No. 4,465,775 to Houts (Vitamin Brand labeled Derivatives for Such Assay); U.S. Pat. No. 5,308,606 to Wilson et al (Method of Treating and/or Diagnosing Soft Tissue Tumors); U.S. Pat. No. 5,405,839 (Vitamin B, Derivative, Preparation Process Thereof, and Use Thereof); U.S. Pat. No. 5,608,060 to Axworthy et al (Biotimidase-Resistant Biotin-DOTA Conjugates); U.S. Pat. No. 5,869,465 to Morgan et al (Method of Receptor Modulation and Uses Therefor); U.S. Pat. No. 5,869,466 to Russell-Jones et al (vitamin B12 Mediated Oral Delivery systems for GCSF). See also Ruma Banerjee, Chemistry and Biochen2istry of B12 John Wiley & Sons, Inc. (1999), and in particular Part II, Section 15 of that book, entitled "Diagnostics and Therapeutic Analogues of Cobalamin," by H. P. C. Hogenkamp, Douglas A. Collins, Charles B. Grissom, and Frederick G. West.

A conjugate comprising a porphyrin-like moiety linked to an anti-tumor drug by way of a cleavable linker has been disclosed by Han (U.S. Pregrant Publication No. 2002/0155999). Protoporphyrin is derivatized with a linker and subsequently reacted with an available functional group of an anti-tumor compound to form the conjugate. The conjugate of Han, however, is adapted for cleavage in the physiological condition surrounding the tumor rather than within the tumor.

While in vivo efficacy is the hallmark of success in anticancer and anti-tumor therapy, efficacy should not come at the cost of excessive systemic toxicity. In fact, it is highly desirable, although frequently untenable, to provide an anticancer or anti-tumor agent possessing increased toxicity toward cancer and tumor cells but decreased systemic toxicity toward the host or subject receiving the agent. A preferred anticancer or anti-tumor agent is one that provides a high kill rate for cancer or tumor cells and a low death rate for the host. The prior art does not disclose or suggest VB12 conjugates possessing reduced systemic toxicity and enhanced efficacy as compared to their corresponding free drugs, yet a need for such conjugates remains.

Accordingly, while the prior art recognizes the potential utility of cobalamin derivatives for the treatment of cancer or tumors, it has not successfully prepared antiproliferative drug 5'-OH conjugates of cobalamin, wherein the drug is attached to the cobalamin by way of a linker that is degradable or hydrolysable with an intracellular enzyme. In particular, the prior art does not disclose the preparation of such a conjugate comprising doxorubicin nor the use of a cobalamin 5'-OH-doxorubicin conjugate for the treatment of tumors or cancer.

SUMMARY OF THE INVENTION

The invention provides an intracellular enzyme cleavable anti-tumor drug and cobalamin conjugate adapted for active transport across a cellular membrane, the conjugate comprising:

a. cobalamin or a cobalamin derivative;
b. a linker covalently bound to the 5'-OH moiety of cobalamin or cobalamin derivative;
c. an anti-tumor drug covalently bound to the linker thereby forming the conjugate, wherein the drug is cleavable from the linker and/or the linker is cleavable from cobalamin by an intracellular enzyme.

Specific embodiments of the invention include those wherein: 1) the conjugate further comprises one or more optional spacers; 2) the conjugate comprises a covalently bound spacer between the linker and 5'-OH moiety of cobalamin; 3) the conjugate comprises a covalently bound spacer between the linker and anti-tumor drug; 4) the anti-tumor drug is selected from the group consisting of doxorubicin, taxol, and other drugs detailed herein; 5) the linker is cleavable from the drug or cobalamin by way of an intracellular enzyme selected from the group of enzyme classes consisting of cathepsin, exoglysidase, endo enzyme, glycosidase, metalloprotease, ribozyme, protease, esterase, and amidase; 6) cobalamin or the cobalamin derivative is selected from those disclosed herein; 7) the conjugate possesses reduced systemic toxicity versus the free anti-tumor drug; 8) the cleavable linker is cleavable by way of a lysosomal enzyme; 9) the cleavable linker is covalently bound at first end to a first spacer and at a second end to a second spacer; 10) the cleavable linker is a cathepsin cleavable peptide; 11) the cleavable linker is a cathepsin B cleavable peptide; and/or 12) the cleavable linker comprises phenylalanine and lysine.

The invention also provides a conjugate of the formula I:

VB-(SPa)$_n$-CL-(SPb)$_m$-DG            Formula I wherein,

CL is a linker that is cleavable from the VB, SPa, SPb and/or DG by way of one or more intracellular enzymes;

VB is cobalamin, or a derivative or analogue thereof, covalently bound to CL or SPa, if present, via the 5'-OH group of the ribose ring of VB;

SPa and SPb are optional spacers independently selected at each occurrence from the group consisting of a covalent bond, divalent functional group, non-peptide residue, or a combination thereof; and DG is an anti-tumor drug;

wherein n and m are independently selected at each occurrence from 0, 1, 2, or 3.

The optional spacers SPa and SPb can be located on either side of the cleavable linker CL. For example, both can be on the VB end or on the DG end of the linker. Suitable spacers and linkers are detailed herein. At each occurrence, the spacers SPa and SPb are independently selected at each occurrence from any of the definitions detailed herein. SPa and SPb can be the same or different. If SPa occurs more than once in the conjugate, its definition is independently selected at each occurrence. Likewise, if SPb occurs more than once in the conjugate, its definition is independently selected at each occurrence.

Another aspect of the invention provides a method of treating a tumor comprising the step of administering to a subject in need thereof a therapeutically effective amount of a conjugate according to the invention, the conjugate being stable enough for delivery to and uptake by a cell. Target therapeutic levels for the conjugate are sufficient to provide a desired clinical effect using recognized protocols in the field of pharmacology. In general, administration of the conjugate can be performed by administering the conjugate approximately according to the same dosing regimen of the free drug. The conjugate can be administered at a molar concentration above or below that of the free drug according the clinical response observed in a subject receiving the conjugate.

The invention also provides a pharmaceutical composition and a dosage form comprising a conjugate according to the invention and at least one pharmaceutical excipient. In specific embodiments, the dosage form is adapted for administration by a route selected from the group consisting of oral, buccal, ocular, otic, rectal, vaginal, sublingual, nasal, pulmonary, parenteral, transdermal. Suitable dosage forms include gel, cream, ointment, pill, tablet, capsule, liquid, suspension, osmotic device, bead, granule, spheroid, particulate, paste, prill, reconstitutable solid, powder, or injectable liquid.

Other features, advantages and embodiments of the invention will become apparent to those skilled in the art by the following description, accompanying examples.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

FIG. 1b depicts a "enzyme cleavage stable" conjugate not made according to the invention, since the linker between VB and DG is not cleavable by an intracellular enzyme.

DETAILED DESCRIPTION OF THE INVENTION

Figure 1A:
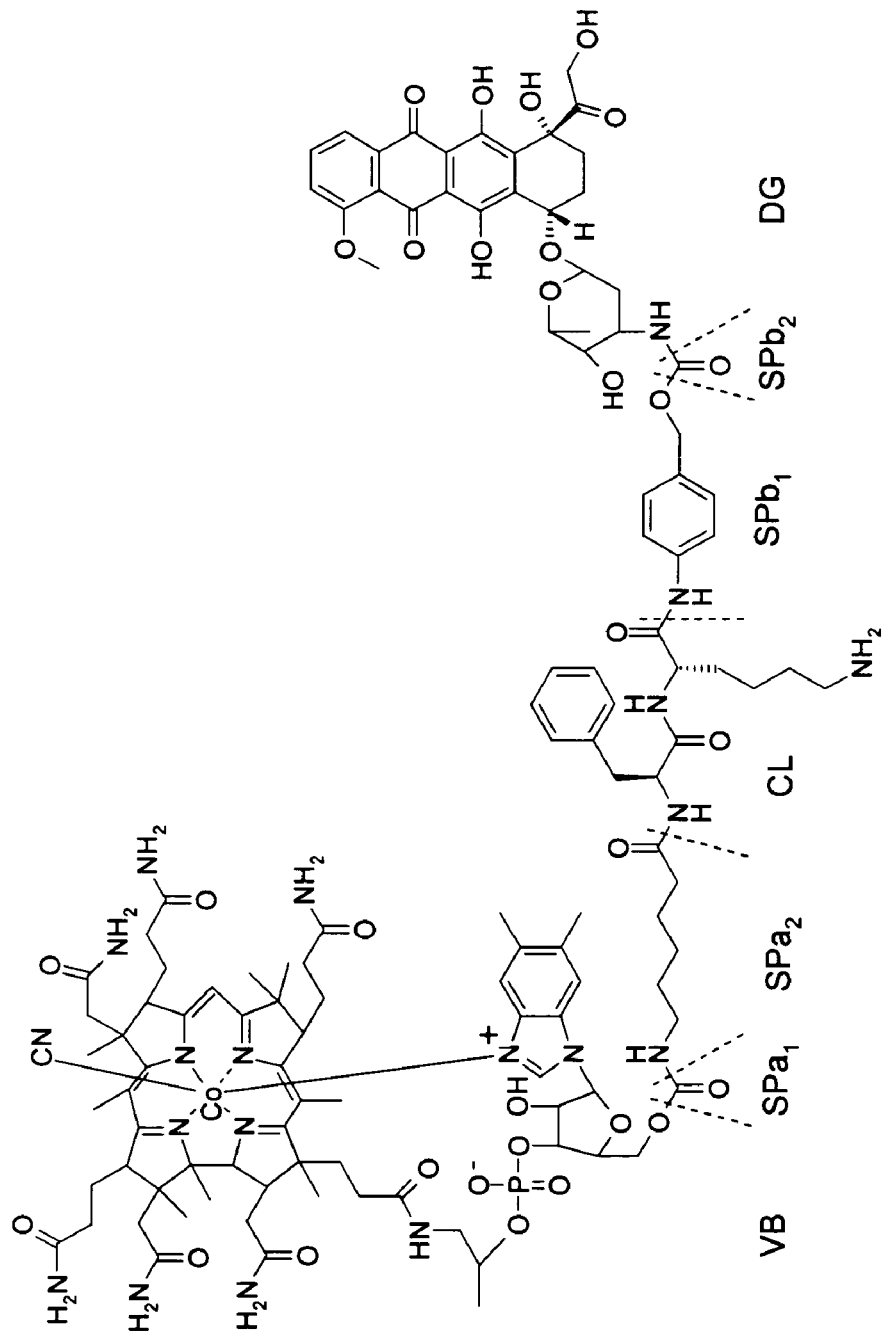
FIG. 1a depicts a first embodiment of the conjugate of the invention.

Some of the abbreviations used herein are defined below:
AA: amino acid
$B_{12}$-5'-OH: cyanocobalamin
CDT: 1,1'-carbonyldi(1,2,4-triazole)
DIC: diisopropylcarbodiimide
DIEA: diisopropylethylamine
DCC: dicyclohexylcarbodiimide
DCU: dicyclohexylurea
DMSO: dimethylsulfoxide
Dox: doxorubicin
EEDQ: 2-ethoxy-1-ethoxycarbonyl-1,2-dihydroquinoline
Fmoc: 9-fluorenylmethoxycarbonyl
HOSu: N-hydroxysuccinimide
HPLC: high performance liquid chromatography
Lys: lysine
MMT: p-methoxyphenyldiphenylmethyl(monomethoxytrityl)
PABOH: p-aminobenzyl alcohol
PABC: p-aminobenzylcarbonyl
PAPC: p-aminophenylcarbonyl
Phe: phenylalanine
PNP: p-nitrophenyl
TMS: trimethylsilyl Doxorubicin hydrochloride was obtained from GensiaSicor Pharmaceuticals as a 2 mg/mL 0.9% saline solution. The solution was adsorbed on a Waters $C_{18}$ Sep-Pak cartridge (P/N WAT043345) and washed with water (three cartridge volumes) to remove sodium chloride. The doxorubicin hydrochloride was eluted with methanol. The methanol was removed by rotary evaporation and the water was removed by lyophilization. AAs and EEDQ were obtained from Novabiochem. Cathepsin B was obtained from Calbiochem (P/N 219364). All other chemicals and solvents were from Acros, Aldrich, Sigma, Fluka, Fisher or VWR and used without further purification unless stated otherwise.

As used herein and unless otherwise specified, the term "cobalamin" is taken to mean cobalamin, an analogue thereof or a derivative thereof. The term cobalamin includes vitamin B12, cyanocobalamin, aquocobalamin, hydroxycobalamin, methylcobalamin, adenosylcobalamin, cyanocobalamin carbanalide, desdimethyl cobalamin, monoethylamide cobalamin, methylamide cobalamin, coenzyme B12, 5'-deoxyadenosylcobalamin, cobamamide derivatives, chlorocobalamin, sulfitocobalamin, nitrocobalamin, thiocyanatocobalamin, benzimidazole derivatives such as 5,6-dichlorobenzimidazole, 5-hydroxybenzimidazole, trimethylbenzimidazole, as well as adenosylcyanocobalamin ((Ade)CN-Cbl), cobalamin lactone, cobalamin lactam and the anilide, ethylamide, monocarboxylic, dicarboxylic and tricarboxylic acid derivatives of VB12, proprionamide derivatives, 5-o-methylbenzylcobalmin, and analogues thereof wherein the cobalt is replaced by another metal atom such as zinc or nickel. The corrin ring of VB12 or its analogues may also be substituted with any substituent which does not completely eliminate its binding to transcobalamin. The above-mentioned compounds are commercially available via suppliers such as Sigma Aldrich Chemical Co., Roche Pharmaceuticals and other chemical commercial suppliers of pharmaceutical finished products, intermediates and starting materials.

A spacer is optional in the compound of Formula 1, the conjugate of the invention. Zero, one or two spacers or a combination of spacers can be included. The spacer serves to adjust the distance between the cobalamin and linker, cobalamin and drug, or linker and drug. The distance from the 5'-O of cobalamin to the point of attachment of the drug to the CL or spacer is sufficient to permit binding of transcobalamin and of an enzyme responsible for cleaving the conjugate. Depending upon the drug being used and the particular form of cobalamin being used, the distance may vary for optimal performance.

Spacers can also be introduced either to improve the transcobalamin affinity of the conjugate or to overcome problems in the coupling of the cobalamin, linker and/or the drug arising from unfavorable steric interactions or to increase the bioactivity of the drug in the conjugate. The spacer compounds may also act as linking agents, being bi-functional compounds with selected functional groups on each end to react with suitable functional groups located on the linker or the cobalamin.

Since the spacers are optional, specific embodiments of the conjugate include: VB-(SPa)$_p$-CL-DG (Formula II), VB-CL-(SPb)$_q$-DG (Formula III), VB-CL-DG (Formula IV), VB-CL-(SPa)$_p$-(SPb)$_q$-DG (Formula V), VB-(SPa)$_p$-(SPb)$_q$-CL-DG (Formula VI), and (VB-(SPa$^2$)(SPa$^1$)-CL-(SPb$^1$)(SPb$^2$)-DG), wherein "p" and "q" are independently selected at each occurrence from 1, 2, or 3.

The spacer SPa or SPb can comprise optionally substituted saturated or unsaturated, branched or linear, C$_{1-50}$ alkylene, cycloalkylene or aromatic group, optionally with one or more carbons within the chain being replaced with N, O or S, and wherein the optional substituents are selected from, for example, carbonyl, carboxy, hydroxy, amino and other groups. When two spacers are included in the conjugate, they are different in structure. A spacer is adapted to cleave from the anti-tumor drug after the CL is cleaved in the target tissue thereby releasing the drug intracellularly in a therapeutically effective form. Spacers that are suitable for inclusion in the conjugate of the invention include those described by Firestone et al. (U.S. Pat. No. 6,214,345) and Katzenellenbogen (J. Med. Chem. (1981), 24(5), pp479-480). These spacers are designed to allow an intracellular enzyme to approach and cleave the linker. They are also designed to cleave from the drug to form the active form of the drug after the linker has been cleaved. A spacer is covalently bound to the CL, DG and VB such that it is sufficiently chemically stable to remain bound thereto until the conjugate is delivered to a target cell or tissue. In a specific embodiment, the spacer is cleaved intracellularly, either by an enzyme or other means, within a target cell or tissue. If a spacer is cleavable, it can be cleaved by the same or a different means as a cleavable linker to which it is attached. Alternatively, the spacer will substantially cleave itself from the cleavable linker and/or anti-tumor drug after the cleavable linker is cleaved intracellularly from VB or SPa. In a specific embodiment, an intracellular enzyme initially releases CL-SPb-DG (or CL-DG) from VB-SPa or VB. The remaining residue CL-SPb-DG (or CL-DG) then cleaves by itself thereby releasing free drug intracellularly. Cleavage need not be solely enzymatic, as it can include additional chemical cleavage provided enzymatic cleavage occurs first.

Suitable extended spacers for conjugation of the drug or cobalamin to the linker include, for example, disuccinimidyl suberate (DSS), bis(sulfosuccinimidyl) suberate (BSS), ethylene glycolbis(succinimidylsuccinate) (EGS), ethylene glycolbis(sulfosuccinimidylsuccinate) (Sulfo-EGS), p-aminophenylacetic acid, dithiobis(succinimidylpropionate) (DSP), 3,3'-dithiobis-(sulfosuccinimidylpropionate) (DTSSP), disuccinimidyl tartarate (DST), disulfosuccinimidyl tartarate (Sulfo-DST), bis[2-(succinimidooxycarbonyloxy)-ethylene]sulfone (BSOCOES), bis[2-(sulfosuccinimidooxycarbonyloxy)-ethylene]sulfone (Sulfo-BSOCOES), dimethyl adipimidate 2HCl (DMA), dimethyl pimelimidate.2HCl (DMP), dimethyl suberimidate.2HCl (DMS).

When the spacer is a divalent functional group it can be attached to the cobalamin, cleavable linker or drug in a forward or reverse direction. Suitable divalent functional groups include —NHNH—, —NH—, —O—, —S—, —SS—, —CH$_2$—, —NHCO—, —CONH—, —CONHNHCO—, —N=N—, —N=CH—, —NHCH$_2$—, —NHN=CH—, —NHNHCH$_2$—, —SCH$_2$—, —CH$_2$S—, —NHCRNH— (R is =O, =S or =NH), —COO—, or —OCO—.

The cleavable linker "CL" is intended to resist breakdown from enzymes in the plasma and optionally gastrointestinal tract of a mammal. The cleavable linker will undergo intracellular cleavage after it is taken up by a cell. The CL is a peptide or non-peptide.

The combination of elements (SPa)$_n$-CL-(SPb)$_m$ of the conjugate, and other embodiments thereof as described herein, together form a "conjugating unit" having a structure as defined by the specific definition of the individual elements SPa, SPb, and CL and the variables n and m. In other words, the "conjugating unit" will be defined by any permissible embodiment of (SPa)$_n$-CL-(SPb)$_m$.

According to a specific embodiment, the conjugating unit of the present invention is made up of a carboxylic acyl unit, and a protein peptide sequence. It may also contain a self-immolating spacer that spaces the drug and the protein peptide sequence.

In a specific embodiment of the conjugate, the conjugating unit is defined as "A-Y-Z-X-W" (Formula XI) in which "A" is a "carboxylic acyl unit", "Y" and "Z" are each amino acids and together form the protein peptide sequence, and "X" and "W" are individualy self-immolating spacers that space the protein peptide and the drug. The conjugating unit A-Y-Z-X-W is a subset of the conjugating unit (SPa)-CL-(SPb)$_m$ and the conjugating unit (VB-(SPa$^2$)(SPa$^1$)-CL-(SPb$^1$)(SPb$^2$)-DG).

Specific embodiments include those wherein:

Y is at least one amino acid selected from the group consisting of alanine, valine, leucine, isoleucine, methionine, phenylalanine, tryptophan and proline, preferably phenylalanine or valine; and Z is at least one amino acid selected from the group consisting of lysine, lysine protected with acetyl or formyl, arginine, arginine protected with tosyl or nitro groups, histidine, ornithine, ornithine protected with acetyl or formyl, and citrulline, preferably lysine, or citrulline.

The protein peptide sequence is specifically tailored so that it can be selectively enzymatically cleaved from the conjugate by one or more proteases in a tumor cell.

The chain length of protein peptide sequence generally ranges from that of a dipeptide to that of a tetrapeptide. However, a protein peptide sequence as long as eight amino acid residues may also be employed.

Suitable exemplary peptide linker groups include by way of example and without limitation Phe-Lys, Val-Lys, Phe-Phe-Lys, D-Phe-L-Phe-Lys, Gly-Phe-Lys, Ala-Lys, Val-Cit, Phe-Cit, Leu-Cit, Ile-Cit, Trp-Cit, Phe-Ala, Gly-Phe-Leu-Gly, Ala-Leu-Ala-Leu, Phe-N$^9$-tosyl-Arg, and Phe-N$^9$ Nitro-Arg.

Numerous specific embodiments of the conjugating unit can be designed and optimized in their selectivity for enzymatic cleavage by a particular tumor-associated protease. Specific embodiment of the conjugating unit include those that are optimized toward hydrolysis by the proteases cathepsin B, C or D.

As noted above, the conjugating unit can employ an intermediate self-immolative (a spacer that removes itself from DG after cleavage of CL without requiring a second enzyme catalyzed cleavage). A self-immolative spacer may be defined as a bifunctional chemical moiety that is capable of covalently linking together two spaced chemical moieties into a normally stable tripartate molecule, releasing one of said spaced chemical moieties from the tripartate molecule by means of enzymatic cleavage; and following said enzymatic cleavage, spontaneously cleaving from the remainder of the molecule to release the other of said spaced chemical moieties. In accordance with the present invention, the self-immolative spacer is covalently linked at a first end to the protein peptide sequence and covalently linked to other end to the DG moiety, so as to space and covalently link together the protein peptide sequence and the drug into a sequence that is stable but which is enzymatically cleavable by a target enzyme at the bond covalently linking the self-immolative spacer and the protein peptide sequence thereby affecting release of the protein peptide sequence. Such enzymatic cleavage, in turn, will activate the self-immolating character of the spacer moiety and initiate substantially spontaneous cleavage of the bond covalently linking the self-immolative spacer to the drug moiety thereby affecting release of the drug in pharmacologically active form.

In the conjugating unit of Formula XI:

X is a self-immolative spacer moiety which spaces and covalently links together the drug and the peptide protein sequence, in which the spacer is linked to the drug moiety via the T moiety and in which the spacer may be represented by the compounds of Formulae (XII), (XIII), (XIV) or (XV):

a) 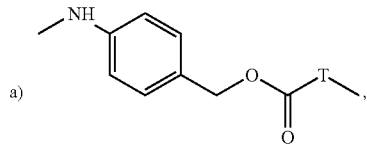 (Formula XII)

in which T is O, NH, N or S;

b) —HN—R$^1$—COT (Formula XIII) in which T is O, NH, N or S, and R$^1$ is C$_1$-C$_5$ alkyl;

c) —NHC(HT)CO$_2$R$^2$-(Formula XIV; *J. Med. Chem.*, 27:1447 (1984)), in which T is O, NH, N or S, and R$^2$ is H or C$_1$-C$_5$ alkyl; or d) 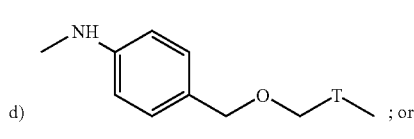 (Formula XV) ; or

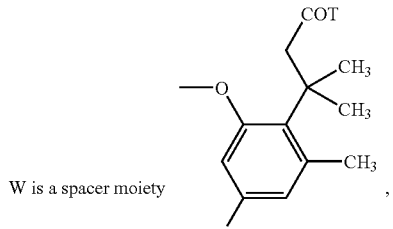 (Formula XVI)

W is a spacer moiety wherein T is O, S or NH, N.

As used herein "C$_1$-C$_5$ alkyl" is taken to mean branched or straight-chain hydrocarbon chain having, unless otherwise noted, one to five carbon atoms, including but not limited to methyl, ethyl, isopropyl, n-propyl, sec-butyl, isobutyl, n-butyl, n-pentyl, isopentyl, sec-pentyl, and other known alkyl groups.

As detailed herein, PABC, GABA (γ-aminobutyric acid in the acyl form), α,α-dimethyl GABA, and β,β-dimethyl GABA are exemplary self-immolative spacers.

In the conjugating unit of Formula (XI), the carboxylic unit "A" can be linked to the VB element via the 5'-O atom of the VB. Exemplary embodiments of the element "A" include:

a) 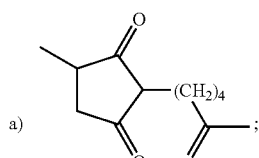

b) 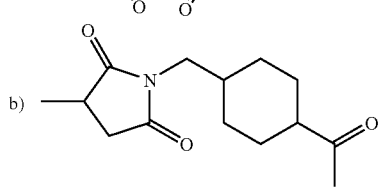

made from succunimidyl 4-(N-maleimidomethyl)-cyclohexane-1-carboxylate (SMCC)(Pierce Catalog p. E-15 (1992));

c) 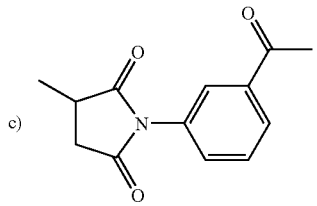

made from m-maleimidobenzoyl-N-hydroxysuccinimide ester (MBS) (Pierce Catalog p. E-16 (1992));

d) 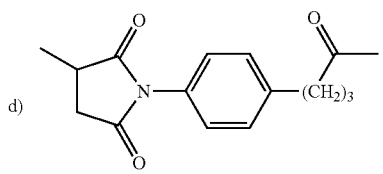

made from succinimidyl 4-(p-maleidophenyl)butyrate (SMPB) (Pierce catalog p. E-18 (1992);

e) 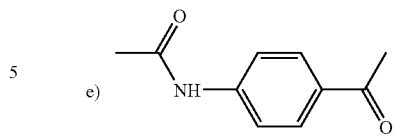

made from N-succinimidyl(4-iodoacetyl)aminobenzoate (SIAB) (Pierce catalog p. E-17 (1992)); or "A" is a compound that is covalently bound to the peptide protein sequence and VB via the 5'-O oxygen atom of the VB. Representative embodiments of the element "A" include by way of example and without limitation:

a) 5'—O—[—(CH$_2$)$_2$—C(=O)—]—;
b) 5'—O—[—CH(CH$_3$)—C$_4$H$_4$—C(=O)—]—; or
c) 5'—O—[—(CH$_2$)$_2$—C(=O)NH—(CH$_2$)$_5$—C(=O)—]—.

The table below details exemplary intracellular enzymes that can be relied upon to cleave the conjugate intracellularly. The list of enzyme classes, specific enzymes and substrates detailed below is not comprehensive, but is merely exemplary of specific embodiments of the same. A conjugate may be adapted for cleavage by other intracellular enzyme families and other specific intracellular enzymes, by providing, within the conjugate, specific substrates suitable for cleavage by those other enzymes.

| FAMILY | ENZYME | SUBSTRATE | PRODUCT/ACTION | LOCATION |
|---|---|---|---|---|
| Cathepsins | Example: Cathepsin B | Phe-LyS | Cleaves 3' of Lys residue | Lysosome |
| Endo enzymes** | Endo H, etc. | GlcNAc–GlcNAc-protein | Cleaves between the GlcNAc residues | Cellular; Mitochondria |
| Glycosidases | Lactase-phlorzin hydrolase | Lactose | D-glu and D-gal | Type I membrane protein in small intestine |
| Glycosidases | Alpha-amylase* | Oligo and polysaccharides: AspGlu substrate | Endohydrolysis of 1,4-alpha-glucosidic linkage in oligo and polysaccharides | Saliva and pancreas secretions |
| Glycosidase | Alpha-mannosidase** | Alpha 1,2 linked alpha D-mannose in the oligosaccharide Man (9) (GlcNAc); needs Asn link | Glycosyl hydrolase; Trims mannose residues in Asn linked oligos | Golgi |
| Furin protease | Furin | Arg-Xaa-Yaa-Arg-Z; Y = Arg or Lys | Arg-Xaa-Yaa-Arg and-Z | ER/Golgi/trans-golgi/possibly lysosome |
| Protease | Granzyme A | Arg-Xaa > Lys-Xaa > Phe-Xaa in small molecule substrates. | Arg + X or Lys + X | endogenous |
| Metalloprotease | Metallendopeptidase N-Arg Dibasic convertase | N-terminus of Arg-dibasic peptides | Arg + Basic AA | Cytosol |
| Ribozyme | Hammerhead | Structure dependent; Recognizes 5'GUC' | Cleaves 3' of C in ribozyme structure | Intracellular, but have been known to degrade in blood |

Enzyme which is secreted. Not specifically cellular*
Enzymes which use a protein substrate as opposed to a peptide structure**

Due to the complex nature of human metabolism, it is possible that a portion of a unit dose containing a conjugate will be cleaved extracellularly after it is administered to a subject. It is intended that the amount of conjugate that is taken up by a cell and subsequently cleaved intracellularly will be sufficient to provide the desired clinical benefit.

FIG. 1 depicts an exemplary conjugate according to the invention. The conjugate, which can be made according to the process of Example 1 comprises doxorubicin bound to a first spacer (SPb) which is bound to a cleavable linker (CL) that is then bound to a second spacer (SPa) which is finally bound to the 5'-OH moiety of the ribose ring of cobalamin (CB). A terminal amine group of the spacer (a first SPa residue; 6-aminohexanoic acid) is bound to the 5'-O of the ribose ring by way of a divalent carbonyl radical (a second SPa residue) thereby forming a carbamate linkage. At the other end of SPa, the carbonyl group of the spacer is bound to the terminal amine of the peptide linker (CL; Phe-Lys-PAB) by way of an amide bond, in particular the terminal amine of phenylalanine residue of the linker. The carboxy terminus end of the linker is bound to the spacer SPb (a first SPb residue; para-aminobenzyl alcohol) by way of an amide linkage. The hydroxyl group of the first SPb is then bound to the primary amine of doxorubicin (DOX) via a divalent carbonyl radical (a second SPb residue). Accordingly, the compound (13) has the following formula: VB-SPa$^2$SPa$^1$-CL-SPb$^1$SPb$^2$-DG (Formula II).

An exemplary synthetic process for the conjugate (13) is detailed in Example 1 below and in FIG. 2. The first part of the synthesis concerns preparation of the cleavable linker Phe-Lys. The second part of the synthesis concerns attachment of the cleavable linker to the first spacer (PABC) and subsequently the anti-tumor drug (DOX). The third part of the synthesis concerns attachment of the second spacer to cobalamin and subsequently, coupling of the second spacer to the N-terminus of the cleavable linker.

Accordingly, Fmoc-Lys is treated with trimethylsilyl chloride to form the carboxyl-protected intermediate Fmoc-Lys(TMS)TMS, which is then and then treated with MMT chloride to form Fmoc-Lys(MMT)TMS which is deprotected during work-up to form the intermediate Fmoc-Lys(MMT) (1). The reactions of this first conversion occur in situ without isolation of any intermediates therein according to the procedure of Dubowchik et al. (*Bioconjugate Chem.* (2002), 13, 855-869). The Fmoc protecting group of the intermediate (1) is removed by treatment with diethylamine to form Lys(MMT) (2). The other key intermediate Fmoc-Phe-OSu (3) is prepared by treating Fmoc-Phe with N-hydroxysuccinimide and DCC. Lys(MMT) and Fmoc-Phe-OSu are coupled in the presence of diisopropylethylamine to form Fmoc-Phe-Lys(MMT) (4). The first portion of the spacer (PAB; SPb$^1$) is attached to the cleavable linker by reacting p-aminobenzyl alcohol with (4) in the presence of ethoxy-1-ethoxycarbonyl-1,2-dihydroquinoline (EEDQ) to form Fmoc-Phe-Lys(MMT)-PABOH (5). The divalent carbonyl portion (SPb$^2$) of the spacer is formed by treating the intermediate (5) with bis(4-nitrophenyl)carbonate (PNP) to form the activated intermediate Fmoc-Phe-Lys(MMT)-PABC-PNP (6). Doxorubicin is then reacted with the activated intermediate (6) to form Fmoc-Phe-Lys(MMT)-PABC-Dox (7). The N-terminus of Phe is deprotected by treatment of the intermediate (7) with diethylamine to form Phe-Lys(MMT)-PABC-Dox (8; CL-SPb$^1$SPb$^2$-DG).

Cyanocobalamin is treated with 1,1'-carbonyldi(1,2,4-triazole) (CDT) to form the triazole activated cyanocobalamin (4; B$_{12}$-5'-OCO-(1,2,4-Triazole), which is then coupled to the spacer (SPa; 6-aminohexanoyl radical) to form the CB-SPa$^2$ residue (10; B$_{12}$-5'-OCONH(CH$_2$)$_5$CO$_2$H). Before coupling this residue to the N-terminus of the cleavable linker, the carboxyl group is activated by treatment of the intermediate (10) with N-hydroxysuccinimide to form the activated intermediate B$_{12}$-5'-OCONH (CH$_2$)$_5$COOSu (11). The two key intermediates (8) and (11) are then reacted to form the protected conjugate (12) (B$_{12}$-5'-OCONH(CH$_2$)$_5$CO-Phe-Lys(MMT)-PABC-Dox, which is then deprotected with dichloroacetic acid to form the conjugate (13) (B$_{12}$-5'-OCONH(CH$_2$)$_5$CO-Phe-Lys-PABC-Dox).

Figure 2:
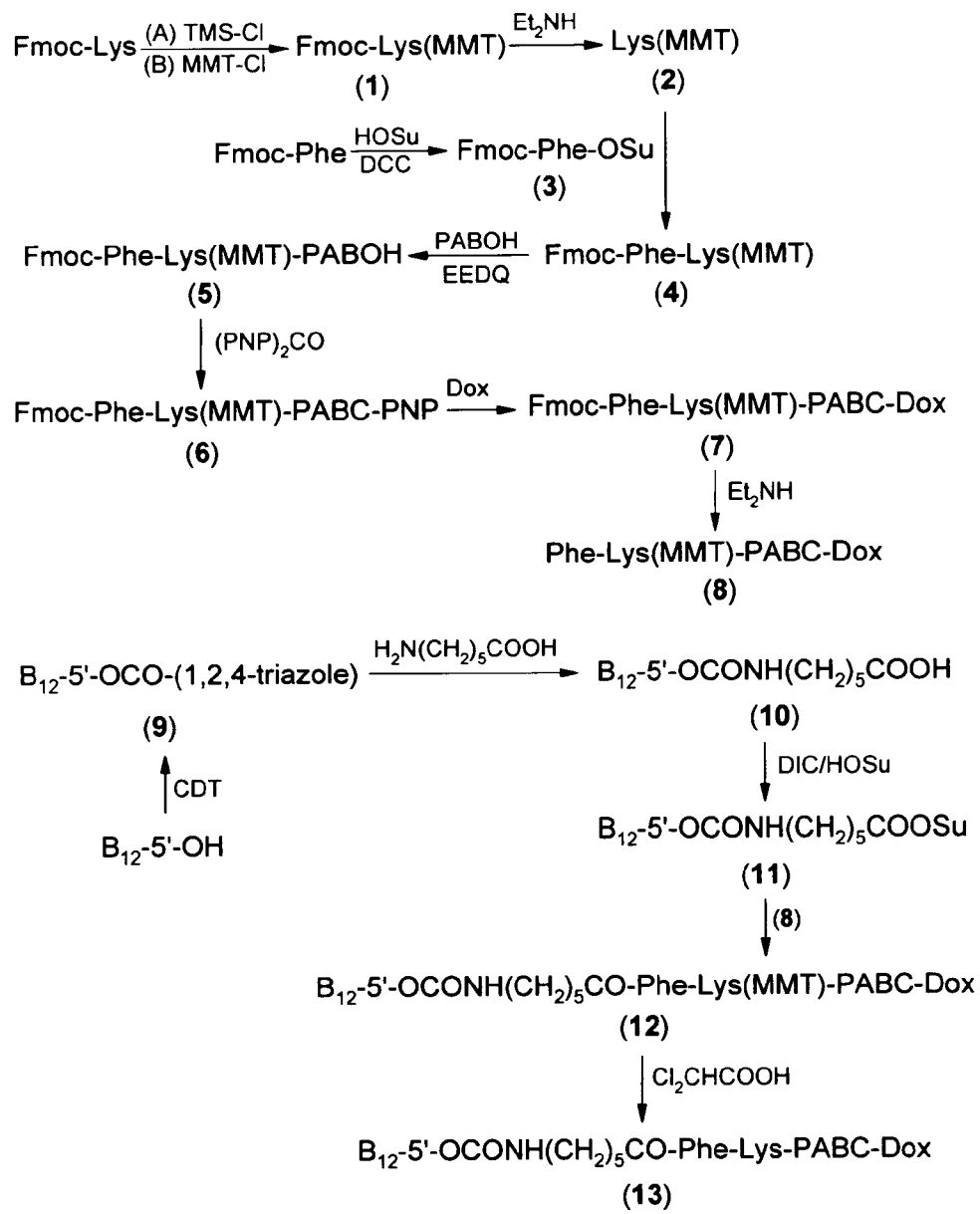
FIG. 2 depicts an exemplary process for the synthesis of a cathepsin B-cleavable doxorubicin-cobalamin conjugate.

More generally, the synthetic scheme depicted in FIG. 2 can be summarized with the following steps:
prepare a protected cleavable linker;
prepare a first residue comprising the cleavable linker and a spacer (SPb);
prepare a second residue comprising the cleavable linker, SPb and an anti-tumor drug (DG);
prepare a third residue comprising cobalamin and a spacer (SPa);
couple the second and third residues to form a conjugate according to the invention.

The second residue can be formed before or after the third residue.

Alternatively, a conjugate of the invention can be prepared according to the synthetic scheme depicted in FIG. 3, which can be generally described as follows. An SPa residue is activated and coupled to a first amino acid (AA$_1$) residue of the CL to form an SPa-AA$_1$ intermediate, which is then activated and reacted with a second amino acid (AA$_2$) residue of the CL to form an SPa-CL intermediate. The SPa-CL intermediate is then activated and reacted with an SPb residue to form an SPa-CL-SPb intermediate that is then activated and coupled to an anti-tumor drug to form an SPa-CL-SPb-DG intermediate. The cobalamin (VB) is activated and coupled with the SPa-CL-SPb-DG intermediate to form VB-SPa-CL-SPb-DG, a compound of the formula I, which optionally comprises one or more protecting groups.

Figure 3:
FIG. 3 depicts an alternate exemplary process for the synthesis of a cathepsin B-cleavable doxorubicin-cobalamin conjugate.

The synthetic scheme of FIG. 3 is more particularly described as follows. Fmoc N-protected 6-aminohexanoic acid is activated with HOSu to form the reactive intermediate (21), which is then reacted with Phe to form Fmoc-NH(CH$_2$)$_5$CO-Phe (22). This intermediate is activated with HOSu to form the reactive intermediate (23) which is subsequently reacted with previously prepared Lys(MMT) (25) for form Fmoc-NH(CH$_2$)$_5$CO-Phe-Lys(MMT) (26). The second spacer PAB is then coupled to the C-terminus end of the linker to form Fmoc-NH(CH$_2$)$_5$CO-Phe-Lys(MMT)-PABOH (27), which is then activated with (PNP)$_2$CO (a divalent carbonyl radical precursor) to form the intermediate Fmoc-NH(CH$_2$)$_5$CO-Phe-Lys(MMT)-PABC-PNP (28). The intermediate (28) is coupled with Dox to form Fmoc-NH(CH$_2$)$_5$CO-Phe-Lys(MMT)-PABC-Dox (29), which N-terminus is then deprotected with diethylamine to form the unprotected intermediate H$_2$N(CH$_2$)$_5$CO-Phe-Lys(MMT)-PABC-Dox (30). The 5'-OH moiety of cobalamin is activated with an electrophilic divalent carbonyl radical precursor, such as CDT, to form B$_{12}$-5'-OCO-(1,2,4-triazole) (31). The two intermediates (30 and 31) are coupled to form a protected conjugate B$_{12}$-5'-OCONH(CH$_2$)$_5$CO-Phe-Lys(MMT)-PABC-Dox (32), which is then deprotected to yield the conjugate (13).

Figure 4A:
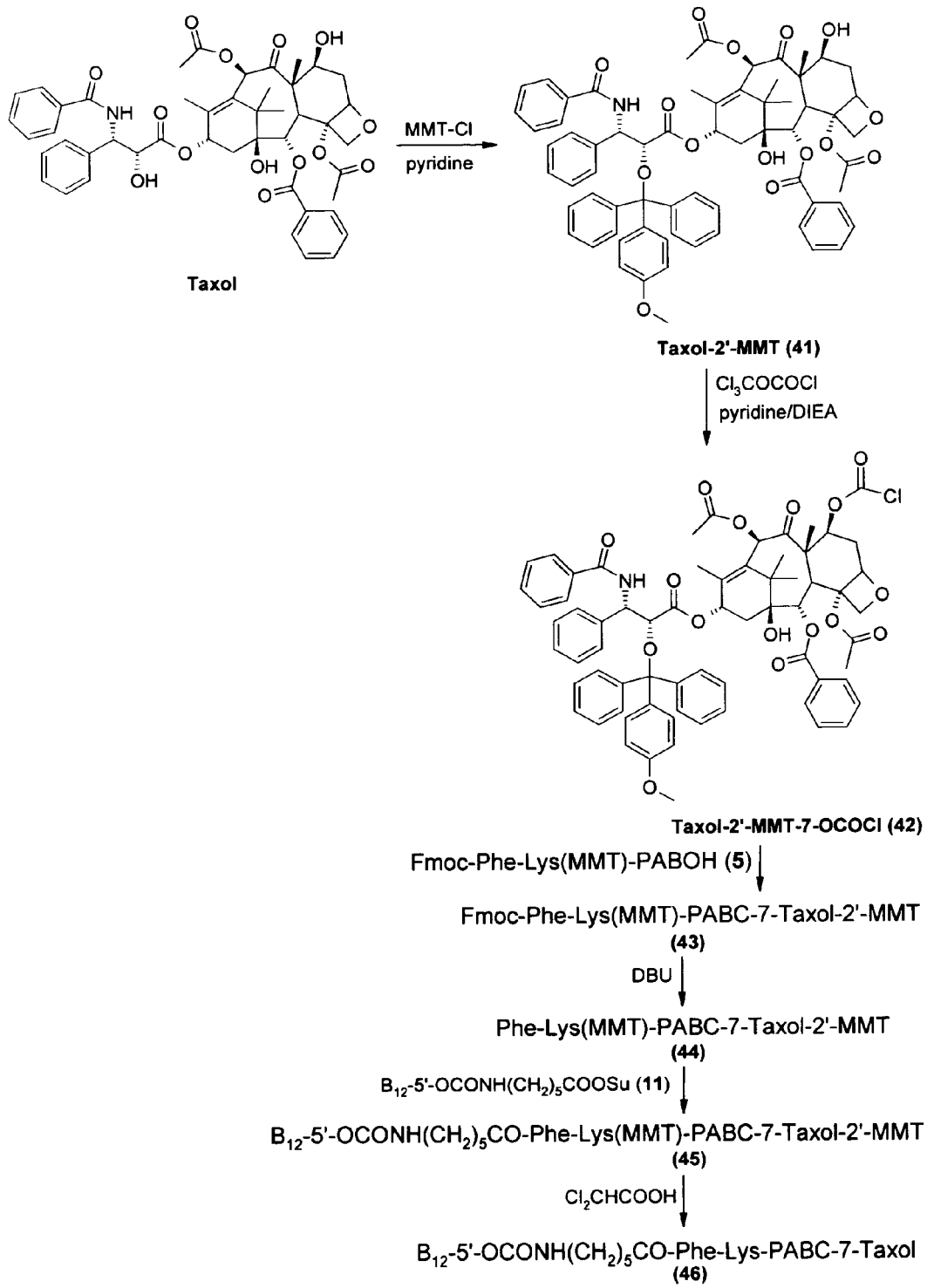
FIGS. 4a-4b depict exemplary processes for the synthesis of a taxol-cobalamin conjugate.

As detailed herein, other anti-tumor drugs can be included in the conjugate of the invention. FIG. 4a depicts a synthetic scheme for the preparation of a conjugate comprising taxol. Since taxol includes three hydroxyl moieties having different reactivities, the conjugate can be formed by coupling a linker to either one of the three depending upon the protecting group strategy employed for taxol. For example, if the 7-OH is derivatized with a protecting group, the taxol can be attached to the spacer or linker by way of the 2'-OH. In the embodiment of FIG. 4a, taxol is treated with MMT chloride in the presence of an organic base, such as pyridine, to tritylate the 2'-hydroxyl moiety thereby forming the partially protected intermediate (41; taxol-2-MMT). The intermediate (41) is then treated with trichloromethoxyoxalyl chloride to protect the 7-OH of taxol and form the protected intermediate (42; taxol-2'-MMT-7-OCOCl). This reactive intermediate is then reacted with the liner-spacer residue (5; Fmoc-Phe-Lys(MMT)-PABOH; CL-SPb) to form the intermediate (43; Fmoc-Phe-Lys(MMT)-PABC-7-taxol-2'-MMT; CL-SPb-Dox). The N-terminus of intermediate (43) is then deprotected, e.g., with DBU, to form the unprotected intermediate (44) to which is coupled the VB-spacer residue (11; VB-SPa) to form the protected conjugate $B_{12}$-5'-OCONH$(CH_2)_5$CO-Phe-Lys(MMT)-PABC-7-taxol-2'-MMT (45). This intermediate is then deprotected, e.g., with dichloroacetic acid, to form the conjugate $B_{12}$-5'-OCONH$(CH_2)_5$CO-Phe-Lys-PABC-7-taxol (46).

The synthetic scheme depicted in FIG. 4a can be generally summarized as follows. An anti-tumor drug is protected as needed and derivatized with a divalent function group capable of accepting the spacer (SPb) or a terminus of the linker (CL). The so derivatized drug is reacted with the spacer (SPb), the linker (CL) or a residue comprising the spacer and linker (CL-SPb) to form an intermediate CL-SPb-DG. The terminus of the linker is deprotected (optionally) and coupled to a reactive cobalamin-spacer residue (VB-SPa) to form a compound of the formula I (VB-SPa-CL-SPb-DG), optionally comprising one or more protecting groups. If present, the protecting groups of the conjugate are optionally removed employing conditions appropriate suitable for their removal as determined according to the type of protecting group(s) being removed.

Figure 4B:
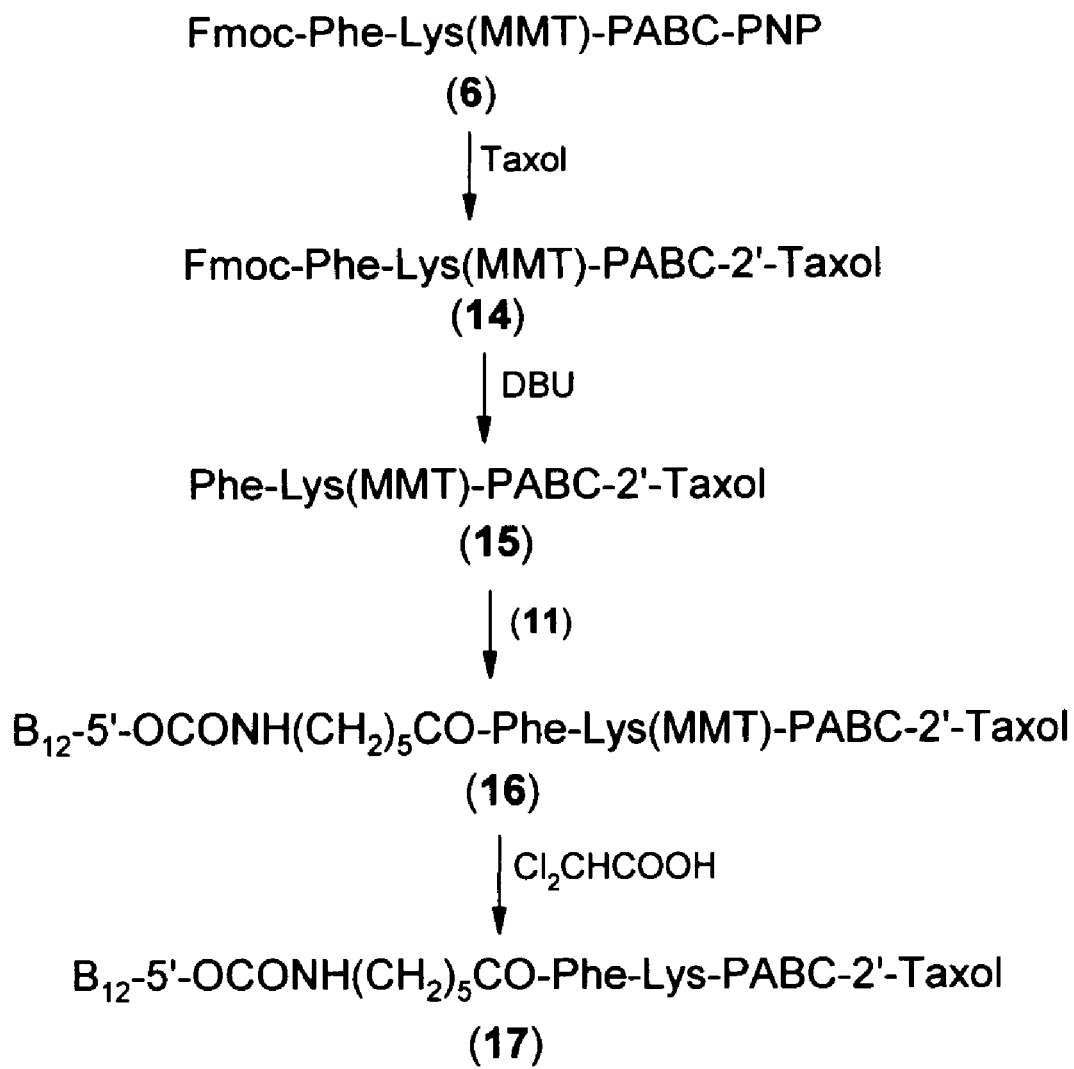

FIG. 4b depicts an alternate synthetic scheme for the preparation of a conjugate comprising taxol according to Example 11. The conjugate of FIG. 4b is different than the conjugate of FIG. 4a, since the conjugates employ different hydroxyl groups of taxol in coupling with a spacer. In this embodiment, the previously prepared reactive intermediate (6) is reacted with taxol in the presence of DMAP (an organic base) thereby coupling to the 2'-hydroxyl moiety of taxol and forming the partially protected intermediate (14; Fmoc-Phe-Lys(MMT)-PABC-2'-Taxol). The Fmoc protecting group is removed by treating the intermediate (14) with DBU (1,8-diazabicyclo[5.4.0]undec-7-ene) to form the partially protected (Lys-protected) intermediate (15; Phe-Lys(MMT)-PABC-2'-Taxol). By reacting this intermediate (15) with the previously formed intermediate (11), the protected conjugate (16; $B_{12}$-5'-OCONH$(CH_2)_5$CO-Phe-Lys(MMT)-PABC-2'-taxol). The N-protected intermediate is then deprotected, e.g., with dichloroacetic acid, to form the unprotected conjugate $B_{12}$-5'-OCONH$(CH_2)_5$CO-Phe-Lys-PABC-2'-taxol (17), which can be isolated as a salt or in free base form.

The synthetic scheme depicted in FIG. 4b can be generally summarized as follows. An unprotected anti-tumor drug is derivatized with an acyl function (SPb$^2$) group bound to an intermediate comprising a spacer (SPb$^1$) covalently bound to a linker (CL). The so derivatized drug is reacted with another intermediate comprising cobalamin covalently bound to a spacer (SPa$^2$)(SPa$^1$) to form of the Formula VII (VB-(SPa$^2$)(SPa$^1$)-CL-(SPb$^1$)(SPb$^2$)-DG) comprising one or more protecting groups. If present, the protecting groups of the conjugate are optionally removed employing conditions appropriate suitable for their removal as determined according to the type of protecting group(s) being removed thereby forming an unprotected form of a compound of the Formula VII.

Figure 5:
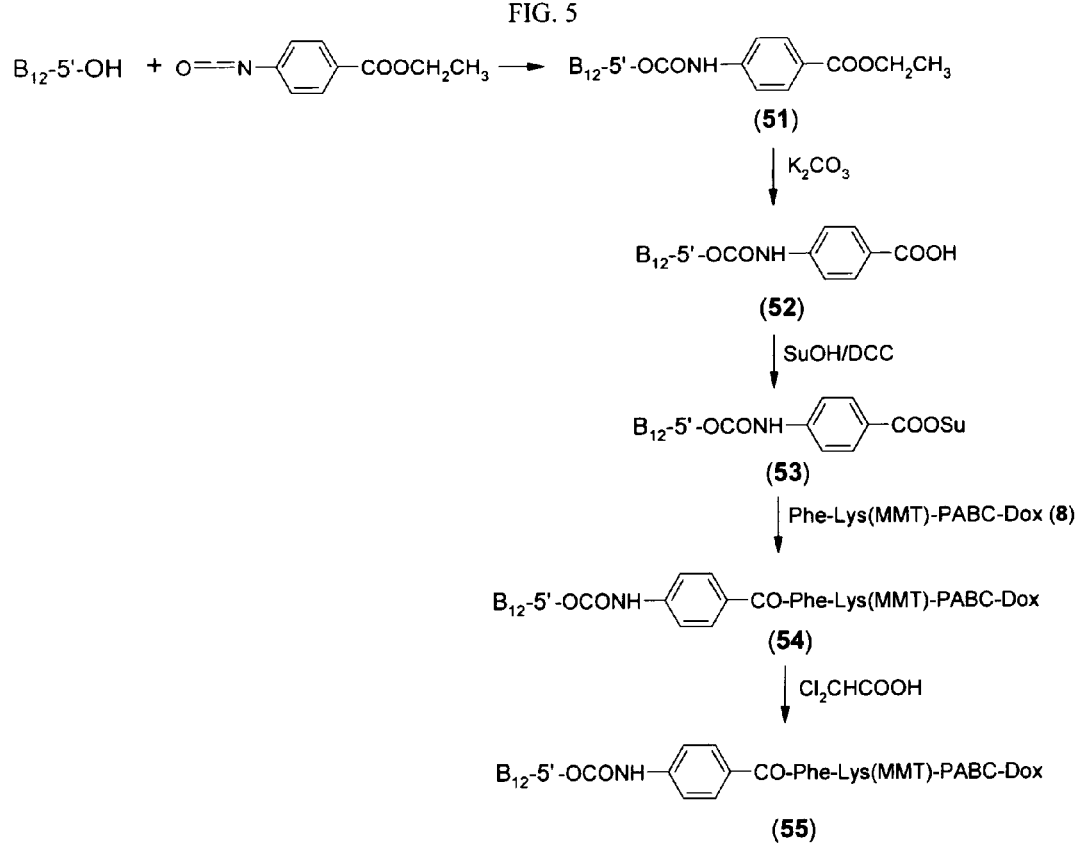
FIG. 5 depicts a doxorubicin-cobalamin conjugate with an alternate linker.

FIG. 5 depicts another alternative synthetic scheme for preparing a conjugate according to the invention. VB12 is reacted with ethyl 4-isocyanatobenzoate to form a cobalamin-spacer intermediate $B_{12}$-5'-OCO-PAPC-OEt (51). This intermediate is then deesterified with potassium carbonate to for the free acid OH (52). The free acid is activate with HOSu and DCC to form the reactive intermediate (53) which is coupled with the linker-spacer-drug intermediate Phe-Lys(MMT)-PABC-Dox (8) to form the protected conjugate $B_{12}$-5'-OCO-PAPC-Phe-Lys(MMT)-PABC-Dox (54). The protected conjugate is then deprotected with dichloroacetic acid to form the conjugate $B_{12}$-5'-OCO-PAPC-Phe-Lys-PABC-Dox (55).

The synthetic strategy depicted in FIG. 5 can be more generally expressed as follows. A cobalamin-spacer residue (VB-SPa) is prepared by coupling cobalamin to a spacer. The cleavable linker CL, or the residue CL-SPb, is attached to the residue to form the intermediate VB-SPa-CL, or VB-SPa-CL-SPb, respectively. If the intermediate VB-SPa-CL is formed, it is further treated to form the intermediate VB-SPa-CL-SPb. The drug is then attached to the VB-SPa-CL-SPb intermediate to form the conjugate VB-SPa-CL-SPb-DG of formula I. The starting materials, residues and intermediates optionally comprise one or more protecting groups as needed. If present, the protecting groups of the conjugate are optionally removed employing conditions appropriate suitable for their removal as determined according to the type of protecting group(s) being removed. In a similar fashion, the protecting groups of the starting materials, residues and intermediates can be added and removed as needed to permit control of the coupling reactions.

In view of the synthetic schemes herein, a synthesis of the conjugate can begin from the cobalamin, the drug, a spacer or the linker. The remaining portions of the conjugate are then coupled sequentially (one, two or three at a time) to form the final conjugate.

Drugs, spacers, linkers and cobalamin (all forms disclosed herein) having more than one reactive functional group are well known. Examples thereof are disclosed herein. During coupling of the various components (VB, SPa, CL, SPb, and DG) of the compound of formula I, it is sometimes necessary to employ protecting group chemistry to protect some of the reactive functional groups while permitting the coupling reactions to occur at other functional groups. To this end, any known protecting groups can be employed provided they are sufficiently stable to perform as needed in the ensuing coupling reactions and to be isolable, if required by the synthetic strategy. Exemplary protecting groups are disclosed herein and include those listed in *Protective Groups in Organic Synthesis* (Greene and Wuts eds., John Wiley & Sons, New York (1991)), *Protective Groups in Organic Chemistry* (Jif MacOmie, ed., Plenum Pub. Corp. (1973)); and "The Peptides: Analysis, Synthesis, Biology, Vol. 3, Academic Press, New York (1981), the disclosures of which is hereby incorporated by reference.

As used herein, the term "amine protecting group" (or "N-protected") refers to any group known in the art of organic synthesis for the protection of amine groups. As used herein, the term "amine protecting group reagent" refers to any reagent known in the art of organic synthesis for the protection of amine groups that may be reacted with an amine to provide an amine protected with an amine protecting group. Exemplary amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10-dioxo-10,10,10,10-tetrahydrothio-xanthyl)]methyloxycarbonyl; 2-trimethylsilyl-ethyloxy-carbonyl; 2-phenylethyloxycarbonyl; 1,1-dimethyl-2,2-dibromoethyloxycarbonyl; 1-methyl-1-(4-biphenylyl)ethyloxycarbonyl; benzyloxycarbonyl; p-nitrobenzyloxycarbonyl; 2-(p-toluenesulfonyl)-ethyloxycarbonyl; m-chloro-p-acyloxybenzyloxycarbonyl; 5-benzyisoxazolyl-methyloxycarbonyl; p-(dihydroxyboryl)benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxy-carbonyl; N'-p-toluenesulfonyl-aminocarbonyl; t-amyloxycarbonyl; p-decyloxybenzyloxy-carbonyl; diisopropylmethyloxycarbonyl; 2,2-dimethoxycarbonylvinyloxycarbonyl; di(2-pyridyl)methyloxycarbonyl; 2-furanylmethyloxy-carbonyl; phthalimide; dithiasuccinimide; 2,5-dimethylpyrrole; benzyl; 5-dibenzylsuberyl; triphenylmethyl; benzylidene; diphenylmethylene; or methanesulfonamide.

As used herein, the term "carboxyl protecting group" refers to any group known in the art of organic synthesis for the protection of carboxyl groups. Examples of carboxyl protecting groups include, but are not limited to, the following: 1) substituted methyl ester type such as methoxymethyl, tetrahydropyranyl, benzyloxymethyl, N-phthalimidomethyl; 2) 2-substituted ethyl ester type such as 2,2,2-trichloroethyl, 2-methylthioethyl, t-butylethyl, cinnamylethyl, benzylethyl, 2-(2'-pyridyl)ethyl; 3) substituted benzyl ester type such as triphenylmethyl, 9-anthrylmethyl, p-nitrobenzyl, 4-picolyl, 2,4,6-trimethylbenzyl; 4) silyl ester type such as trimethylsilyl, t-butyldimethylsilyl, phenyldimethylsilyl; 5) miscellaneous type such as oxazole, orthoester; 6) amides type such as N,N-dimethyl, piperidinyl, pyrrolindinyl; and 7) hydrazide type such as alkylated hydrazides.

As used herein, the term "hydroxy protecting group" (or "O-protected") refers to any group known in the art of organic synthesis for the protection of hydroxyl groups. As used herein, the term "hydroxy protecting group reagent" refers to any reagent known in the art of organic synthesis for the protection of hydroxy groups which may be reacted with an hydroxy to provide an hydroxy group protected with an hydroxy protecting group. The hydroxy protecting groups are base-stable and can include, but are not limited to acyl types, aromatic carbamate types and alkyl types. Exemplary are methyl, methoxymethyl (MOM), methylthiomethyl, benzyloxymethyl, t-butoxymethyl, 2-methoxyethoxymethyl, 2,2,2-trichloroethoxymethyl, 2-(trimethylsilyl) ethoxymethyl (SEM), tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

Suitable hydroxy protecting groups may include the following protecting groups as ethers: tetrahydropyranyl, triphenylmethyl, benzyl, tetrahydrofuranyl, allyl, methoxymethyl (MOM), benzyloxymethyl, p-methoxybenzyloxymethyl, 2-trimethylsilylethoxymethyl (SEM), t-butoxymethyl, methylthiomethyl, 2-methoxyethoxymethyl, trichloroethoxymethyl, t-butyl, p-methoxybenzyl, t-butyldimethylsilyl, o-nitrobenzyl, p-methoxyphenyldiphenylmethyl, p-nitrobenzyl, triisopropylsilyl, t-butyldiphenylsilyl.

As used herein, the term "sulfhydryl protecting group" (or "O-protected") refers to any group known in the art of organic synthesis for the protection of sulfhydryl groups. As used herein, the term "sulfhydryl protecting group reagent" refers to any reagent known in the art of organic synthesis for the protection of sulfhydryl groups which may be reacted with a sulfhydryl to provide a sulfhydryl group protected with a sulfhydryl protecting group. Suitable sulfhydryl protecting groups include another sulfhydryl-containing compound capable of forming a disulfide bond with the sulfhydryl group being protected, and others disclosed in *Protective Groups in Organic Synthesis* (Greene and Wuts eds., John Wiley & Sons, New York (1991)), *Protective Groups in Organic Chemistry* (Jif MacOmie, ed., Plenum Pub. Corp. (1973)).

As used herein, the term "ketone protecting group" (or "O-protected") refers to any group known in the art of organic synthesis for the protection of ketone groups. As used herein, the term "ketone protecting group reagent" refers to any reagent known in the art of organic synthesis for the protection of ketone groups which may be reacted with a ketone to provide a ketone group protected with a ketone protecting group. Suitable ketone protecting groups include a cyclic acetal, and *Protective Groups in Organic Synthesis* (Greene and Wuts eds., John Wiley & Sons, New York (1991)), *Protective Groups in Organic Chemistry* (Jif MacOmie, ed., Plenum Pub. Corp. (1973)).

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When any variable (for example, R, m, etc.) occurs more than one time in any constituent or formula for a compound, its definition on each occurrence is independent of its definition at every other occurrence. Thus, for example, if a group is shown to be substituted with 0-3 R, then said group may optionally be substituted with up to three R, and R at each occurrence is selected independently from the defined list of possible R. Also, combinations of substituents and/or variables are permissible only if such combinations result in stable compounds. By stable compound or stable structure it is meant herein a compound that is sufficiently robust to survive isolation to a useful degree of purity from a reaction mixture. Similarly, by way of example, for the group —C(R)—, each of the two R substituents on C is independently selected from the defined list of possible R.

A conjugate of the invention is useful for treatment or development of treatments for cancers of any type, including solid tumors and leukemias, such as: apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, Merkel cell, mucinous, non-small cell lung, oat cell, papillary, scirrhous, bronchiolar, bronchogenic, squamous cell, and transitional cell), histiocytic disorders, leukemia (e.g., B cell, mixed cell, null cell, T cell, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia, and for treatment of other conditions in which cells have become immortalized or transformed. The conjugate can be administered in combination with other treatment modalities, such as chemotherapy, cryotherapy, hyperthermia, radiation therapy, and the like.

The term "controlling the growth", as used herein, means slowing, interrupting, arresting, or stopping the growth and metastases of a proliferating tumor in a warm blooded animal; it being understood that treatment (controlling the growth of a tumor) in a warm blooded animal with a conjugate, either with or without the added effects of another cytotoxic anti-tumor agent may not provide a "cure" for the tumor in the sense that necessarily the tumor tissue is destroyed or totally eliminated. Experimentally, however, some tumor tissues have been completely eliminated.

It is generally known that anti-tumor agents can be administered to a patient either individually or in combination. Additionally, anti-tumor agents can be used in conjunction with other anti-tumor therapies. For example, an anti-tumor agent can be administered in conjunction with surgical excision of the tumor or with radiation therapy, immunotherapy, or local heat therapy. When such combination therapy is employed for the treatment of a tumor, the anti-tumor agent may be administered at a dosage known in the art to be effective for treating the tumor. Alternatively, when more than one anti-tumor agent is used for therapy, one or both of the agents may produce an additive or synergistic effect with the other agent against a particular tumor. Thus, when such combination anti-tumor therapy is used, the dosage of one or both of the anti-tumor agents administered may be less than that administered when the anti-tumor agent is used alone. The anti-tumor agents in combination may, therefore, be administered at a lower dosage level or at less frequent intervals as compared to when used alone.

The anti-tumor drug (DG), also known as a chemotherapeutic agent, is a compound that has biological activity against one or more forms of cancer or tumor and that can be linked to the cleavable linker (CL) or optional spacer (SPb) without excessive loss of efficacy. A suitable anti-tumor drug includes an antineoplast, androgen inhibitor, antibiotic, antiestrogen, antimetabolite, cytotoxic agent, immunomodulator, nitrogen mustard, steroid, alkylating agent, antimitotic agent, plant alkaloid, topoisomerase I inhibitor, topoisomerase II inhibitor, biological product, DNA damaging agents, anti-metabolites, natural products and their analogs, hormones, antagonists enzyme inhibitors, other classes/types of anti-tumor agents, protein or polypeptide possessing a desired biological activity, others known to those of skill in the art of tumor therapy and combinations thereof.

Compounds that are exemplary of the suitable anti-tumor compounds of the invention are detailed in the lists below. The tumor(s) against which an anti-tumor compound has recognized efficacy (cytotoxicity) is enclosed in parentheses. Although, the free form of the anti-tumor drugs set forth below are known to be active against the indicated tumors, the conjugate of the invention can have a similar, different, broader or narrower scope of activity. Accordingly, the anti-tumor activity of the conjugate is not necessarily limited to just those tumors indicated for a corresponding free drug.

Nitrogen Mustards: Mechlorethamine (Hodgkin's disease, non-Hodgkin's lymphomas), Cyclophosphamide Ifosfamide (acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas), Melphalan (L-sarcolysin) (multiple myeloma, breast, ovary), Chlorambucil (chronic lymphoctic leukemia, primary macroglobulinemia, Hodgkin's disease, non-Hodgkin's lymphomas).

Ethylenimines and Methylmelamines: Hexamethylmelamine (ovary), Thiotepa (bladder, breast, ovary).

Alkyl Sulfonates: Busulfan (chronic granuloytic leukemia).

Nitrosoureas: Carmustine (BCNU) (Hodgkin's disease, non-Hodgkin's lymphomas, primary brain tumors, multiple myeloma, malignant melanoma), Lomustine (CCNU) (Hodgkin's disease, non-Hodgkin's lymphomas, primary brain tumors, small-cell lung), Semustine (methyl-CCNU) (primary brain tumors, stomach, colon), Streptozocin (streptozocin) (malignant pancreatic insulinoma, malignant carcinoin).

Triazenes: Dacarbazine (DTIC; dimethyltriazenoimidazolecarboxamide-) (malignant melanoma, Hodgkin's disease, soft-tissue sarcomas).

Folic Acid Analogs: Methotrexate (amethopterin) (acute lymphocytic leukemia, choriocarcinoma, mycosis fungoides, breast, head and neck, lung, osteogenic sarcoma).

Pyrimidine Analogs: Fluorouracil (5-fluorouracil; 5-FU) Floxuridine (fluorodeoxyuridine; FUDR) (breast, colon, stomach, pancreas, ovary, head and neck, urinary bladder, premalignant skin lesions) (topical), Cytarabine (cytosine arabinoside) (acute granulocytic and acute lymphocytic leukemias).

Purine Analogs and Related Inhibitors: Mercaptopurine (6-mercaptopurine; 6-MP) (acute lymphocytic, acute granulocytic and chronic granulocytic leukemia), Thioguanine (6-thioguanine: TG) (acute granulocytic, acute lymphocytic and chronic granulocytic leukemia), Pentostatin (2'-deoxycyoformycin) (hairy cell leukemia, mycosis fungoides, chronic lymphocytic leukemia).

Vinca Alkaloids: Vinblastine (VLB) (Hodgkin's disease, non-Hodgkin's lymphomas, breast, testis), Vincristine (acute lymphocytic leukemia, neuroblastoma, Wilms' tumor, rhabdomyosarcoma, Hodgkin's disease, non-Hodgkin's lymphomas, small-cell lung).

Epipodophyl-lotoxins: Etoposide (testis, small-cell lung and other lung, breast, 25Hodgkin's disease, non-Hodgkin's lymphomas, acute granulocytic leukemia, Kaposi's sarcoma), Teniposide (testis, small-cell lung and other lung, breast, Hodgkin's disease, non-Hodgkin's lymphomas, acute granulocytic leukemia, Kaposi's sarcoma).

Antiproliferatives/antibiotics: Dactinomycin (actinonmycin D) (choriocarcinoma, Wilms' tumor rhabdomyosarcoma, testis, Kaposi's sarcoma), Daunorubicin (daunomycin; rubidomycin) (acute granulocytic and acute lymphocytic leukemias), Doxorubicin (soft tissue, osteogenic, and other sarcomas; Hodgkin's disease, non-Hodgkin's lymphomas, acute leukemias, breast, genitourinary thyroid, lung, stomach, neuroblastoma), Bleomycin (testis, head and neck, skin and esophagus lung, and genitourinary tract, Hodgkin's disease, non-Hodgkin's lymphomas), Plicamycin (mithramycin) (testis, malignant hypercalcema), Mitomycin (mitomycin C) (stomach, cervix, colon, breast, pancreas, bladder, head and neck).

Enzymes: L-Asparaginase (acute lymphocytic leukemia).

Biological Response Modifiers: Interferon-alfa (hairy cell leukemia, Kaposi's sarcoma, melanoma, carcinoid, renal cell, ovary, bladder, non Hodgkin's lymphomas, mycosis fungoides, multiple myeloma, chronic granulocytic leukemia).

Estrogens: Diethylstibestrol Ethinyl estradiol (breast, prostate)

Antiestrogen: Tamoxifen (breast).

Androgens: Testosterone propionate Fluxomyesterone (breast).

Antiandrogen: Flutamide (prostate).

Gonadotropin-Releasing Hormone Analog: Leuprolide (prostate).

Platinum Coordination Complexes: Cisplatin (cis-DDP) Carboplatin (testis, ovary, bladder, head and neck, lung, thyroid, cervix, endometrium, neuroblastoma, osteogenic sarcoma).

Anthracenedione: Mixtozantrone (acute granulocytic leukemia, breast).

Substituted Urea: Hydroxyurea (chronic granulocytic leukemia, polycythemia vera, essential thrombocytosis, malignant melanoma).

Methylhydrazine Derivative: Procarbazine (N-methylhydrazine, M1H) (Hodgkin's disease).

Adrenocortical Suppressant: Miotane (o,p'-DDD) (adrenal cortex), Aminoglutethimide (breast).

Adrenorticosteriods: Prednisone (acute and chronic lymphocytic leukemias, non-Hodgkin's lymphomas, Hodgkin's disease, breast).

Progestins: Hydroxprogesterone caproate, Medroxyprogersterone acetate, Megestrol acetate (endometrium, breast A conjugate according to the invention can be administered alone or in combination with one or more anti-tumor agents. Illustrative examples of cytotoxic anti-tumor agents that can be used in combination with a conjugate according to the invention include any agent known to possess cytotoxicity and efficacy against cancer cells.

The conjugate of the invention comprises an anti-tumor drug that comprises a functional group to which the linker or spacer can be covalently bound. Otherwise, the anti-tumor drug can be derivatized to comprise such a functional group. One skilled in the art may make chemical modifications to the desired compound in order to make reactions of that compound more convenient for purposes of preparing conjugates of the invention. Essentially any anti-tumor drug is suitable for conjugation include the invention provided the drug includes or can be derivatized to include at least one functional group by which a spacer or the cleavable linker can be covalently bound. A functional group of the anti-cancer drug by which the conjugate can be form can selected from a primary or secondary amine, hydroxyl, sulfhydryl, carboxyl, hydrazide, nitrile, aldehyde or a ketone. Otherwise, the drug may comprise a derivatizable site, such as an aromatic carbon, an unsaturated bond or a carbon adjacent an unsaturated bond.

Representative amino-containing drugs include for example and without limitation Acivicin, Ametantrone, aminopterin, 9-aminocamptothecin, $N^8$-acetylspermidine, actinomycin, Azotomycin, Bisnafide, bleomycin, Carubicin, 1-(2-chloroethyl)1,2-dimethanesulfonyl hydrazide, Crisnatol, daunorubicin, doxorubicin, Dezaguanine, Eflornithine, Elsamitrucin, Epirubicin, Esorubicin, Exatecan, Idarubicin, Melphalan, Mercaptopurine, mitomycin A, mitomycin C, Mitoxantrone, Nocodazole, Peldesine, Peplomycin, Puromycin, Talisomycin, Thiamiprine, Thioguanine, Vapreotide, Zorubicin, Aminoglutethimide, Azacitidine, Bropirimine, Cytarabine, Dactinomycin, Edatrexate, Etoprine, Fenretinide, Fludarabine, Gemcitabine, Methotrexate, Metoprine, Piritrexim, Porfiromycin, Triciribine, Trimetrexate and analogues and derivatives thereof.

Representative alcohol (hydroxyl)-containing drugs include for example and without limitation auguidine, N-(5, 5-diacetoxypentyl)doxorubicin, Aclarubicin, Ametantrone, Apaziquone, Azacitidine, Bicalutamide, Calusterone, camptothecin, Carubicin, Carzelesin, Crisnatol, Cytarabine, 1,8-dihydroxy-bicyclo[7.3.1]trideca-4,9-diene-2,6-diyne-13-one (U.S. Pat. No. 5,198,560), Elsamitrucin, Epirubicin, esperamicin, Esorubicin, etoposide, Exatecan, Fenretinide, Floxuridine, Fludarabine, Flurocitabine, Fostriecin, Gemcitabine, Hydroxyurea, Idarubicin, Lentinan, Leuprolide, Maytansine, Menogaril, Mitoxantrone, Motexafin gadolinium, morpholine-doxorubicin, Peplomycin, Plicamycin, podophyllotoxin, Prednimustine, Puromycin, Pyrazofurin, Riboprine, Streptozocin, taxol, Teniposide, Tiazofurin, Topotecan, Triciribine, Triptorelin, Uredepa, vincristine, vinblastine, Vindesine, Vinglycinate, Vinrosidine, Vinzolidine, Zorubicin, Bizelesin, Droloxifene, Fenretinide, Mycophenolic acid, Masoprocol, Temoporfin, Topotecan and analogues and derivatives thereof.

Representative sulfhydryl-containing drugs include for example and without limitation esperamicin and 6-mercaptopurine and analogues and derivatives thereof.

Representative carboxyl-containing drugs include for example and without limitation Acivicin, Azotomycin, Brequinar, butyric acid, Carbetimer, camptothecin (ring-opened form of the lactone), Chlorambucil, Edatrexate, Eflornithine, Melphalan, methotrexate, Mycophenolic acid, retinoic acid, Thioguanine, Verteporfin, and analogues and derivatives thereof.

Representative aldehyde or ketone-containing drugs for example and without limitation Aclarubicin, anguidine, anthracyclines, Calusterone, Carubicin, doxorubicin, Dromostanolone, Epirubicin, Esorubicin, Idarubicin, Megestrol, Nocodazole, Oxisuran, Plomestane, Prednimustine, Testolactone, Thioguanine, Trestolone, and analogues and derivatives thereof.

Representative hydrazine-containing drugs include for example and without limitation procarbazine.

When, in the treatment of a neoplastic disease, a conjugate is administered in combination with a cytotoxic agent, the therapeutic effect of the cytotoxic agent may be potentiated. The remission produced by the cytotoxic agent may be enhanced and regrowth of the tumor tissue may be slowed or prevented. Use of such combination therapy therefor allows smaller doses or fewer individual doses of the cytotoxic agent to be employed. Thus, the detrimental and/or debilitating side effects of the cytotoxic agent are minimized while, at the same time, the anti-tumor effects are enhanced. The term "combination therapy" contemplates the administration of a conjugate prior to the beginning of therapy with a cytotoxic agent, concomitantly with such therapy, or during the period of time following cessation of such therapy.

According to specific embodiments of the invention, a patient is treated with a conjugate on a 1-10 times daily, every other day, semi-weekly, weekly, biweekly, monthly, bimonthly or semi-annual basis. Treatment with the conjugate can be continued for a period of, for example, 1 to 365 days. As noted above, the mode of administration or dosing regimen for the conjugate can approximate that of the corresponding free drug. In one embodiment, the conjugate provides an enhanced clinical benefit over the free drug. A modified method of the invention includes periodic and spaced apart administration of the conjugate. For example, the conjugate can be administered repeatedly over a period of time until the desired clinical endpoint is achieved. A treating physician will be able to determine the desired clinical endpoint using methods readily available in the art of anti-tumor therapy. In a specific embodiment, a first course of the conjugate in administered and the subject is observed for a first period of time. A second course of the conjugate can then be administered beginning at a second and spaced apart period of time. The time interval between the first and second course can be as noted above.

When such combination therapy results in remission of the tumor, and all tumor cells are not destroyed, regrowth of the tumor may be prevented or slowed indefinitely by continued or repeat treatment with the conjugate or another anti-tumor drug. A physician in each case, taking into account the condition of the individual patient, can determine effective and non-toxic dosages.

The conjugate can be administered via various routes detailed herein to a patient to achieve the desired effect. The amount of compound administered will vary over a wide range and can be any effective amount. Depending upon the patient to be treated, the severity of the condition being treated, the mode of administration, the dosing regimen, patient health, patient response and the particular conjugate employed, the effective amount of compound administered will vary. As a guide to initial therapy with a conjugate, consideration is taken of the dosage typically administered for the free (unconjugated) drug, such that the initial dose of conjugate will approximate (0.5 to 2.0 times) the molar amount of free drug. For example if the free drug is administered at a dose of about 0.1 mmole per kg of body weight per day, then the conjugate can be initially administered at a dose of about 0.05 to 0.2 mmole per kg of body weight per day. This guideline for administration of a conjugate can be followed for conjugates for which the actual therapeutic dose is unknown but for which the typical therapeutic dose of the corresponding free drug is. The optimal dose of a conjugate can range from about 0.001 to about 100 times, about 0.01 to about 10 times, about 0.01 to about 2 times, or about 0.1 to about 4 times the molar amount of corresponding unconjugated anti-tumor drug.

As used herein the term patient is taken to mean warm blooded animals such as mammals, for example, dogs, rats, mice, cats, guinea pigs, horses, bovine cows, sheep, and humans.

The efficacy of the conjugate for control the growth rate of proliferating tumor tissue can be assessed in standard in vitro and in vivo animal tumor models. For example, the anti-tumor effect of the conjugate can be demonstrated in the following animal tumor models: (a) L1210 leukemia in mice; (b) EMT6 tumor in Balb/C mice; (c) 7,12-dimethylbenzanthracene-induced (DMBA-induced) mammary tumor in rats; (d) Morris 7288C or 5123 hepatoma in Buffalo rats; (e) and others. In addition, the anti-tumor effect of the conjugate in combination with various cytotoxic agents can be demonstrated in the same or other models.

The conjugate (13) was evaluated in an in vitro cell culture assay in a number of different cell types to establish its activity against cancer and tumor cell lines. The percent of viable cells remaining in vitro after treatment with varying concentrations of doxorubicin or the conjugate (indicated as CobalaRubicin 200) was determined. Positive anticancer or anti-tumor activity is indicated by a reduction in the number of viable cells after a given incubation period. Generally, increasing the concentration of drug in vitro results in a higher kill rate of cells and thus in a lower percentage of cell viability. Equimolar concentrations of drug are compared in determining activity of the free drug versus the conjugate.

Figure 6A:
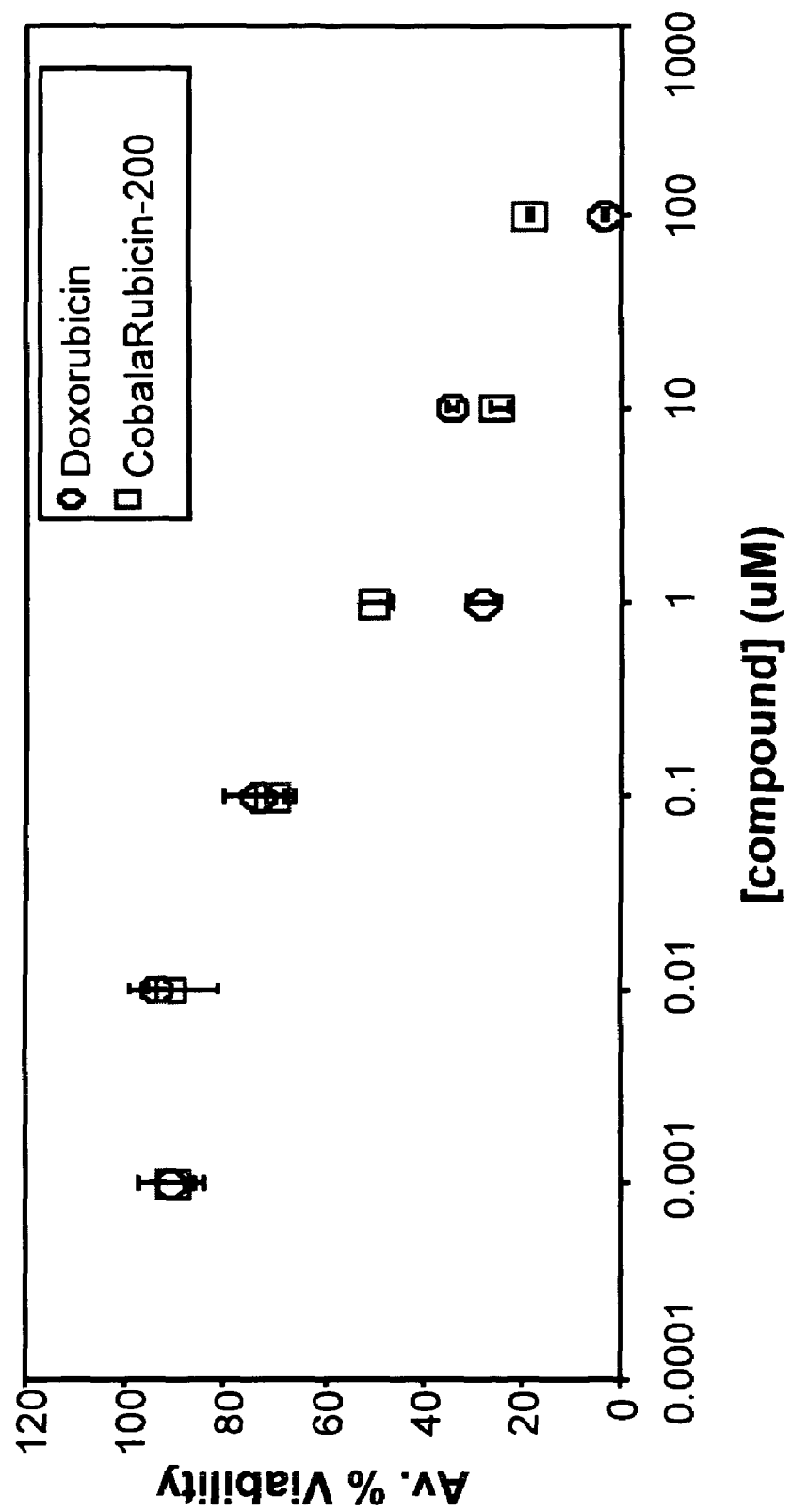
FIG. 6a depicts a chart of the in vitro comparison of free doxorubicin versus a doxorubicin-cobalamin conjugate against MCF-7 cells.
Figure 6B:
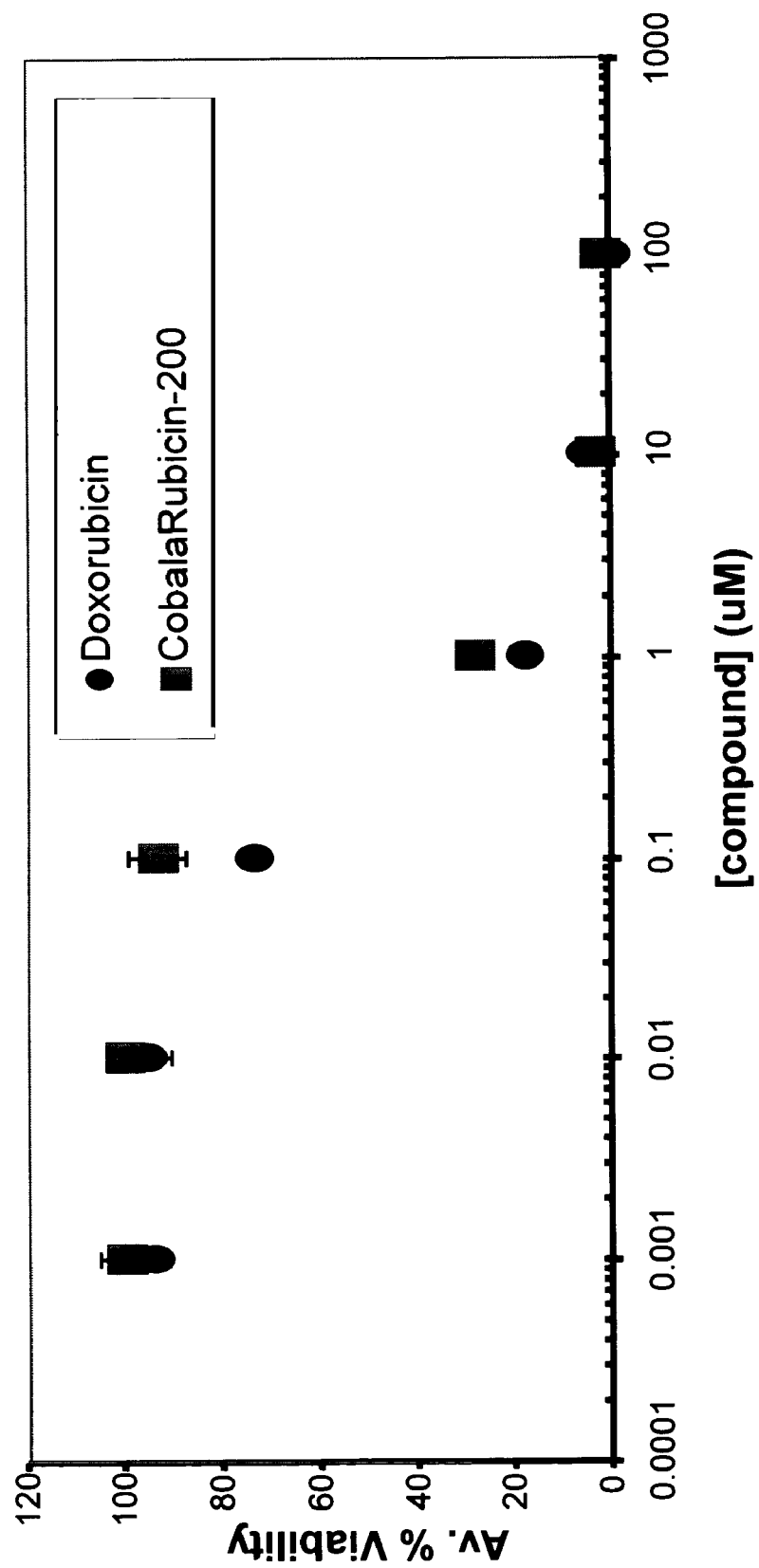
FIG. 6b depicts a chart of the in vitro comparison of free doxorubicin versus a doxorubicin-cobalamin conjugate against SK-BR-3 cells.
Figure 6C:
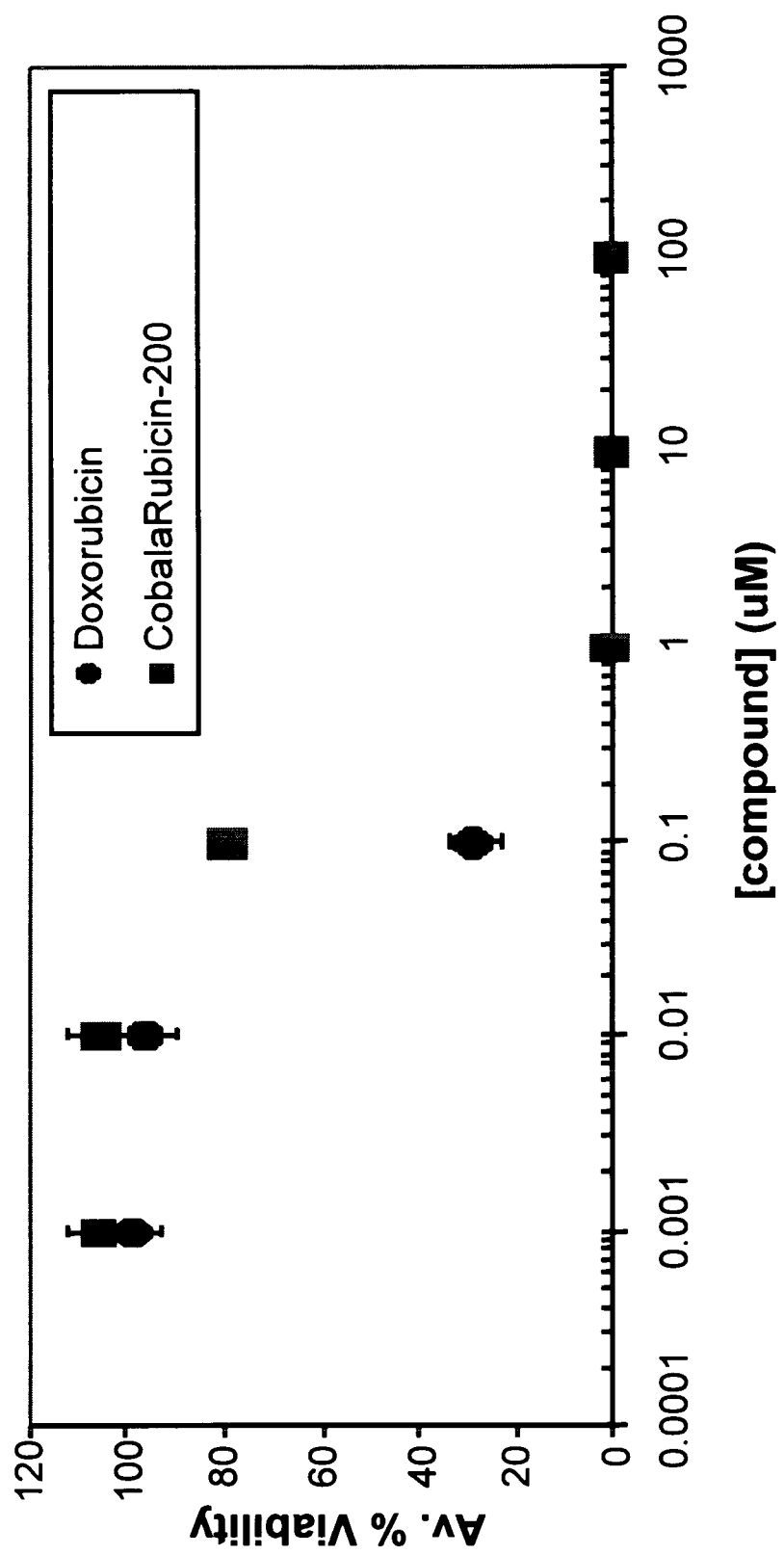
FIG. 6c depicts a chart of the in vitro comparison of free doxorubicin versus a doxorubicin-cobalamin conjugate against HL-60 (promyelocytic leukemia) cells.
Figure 6D:
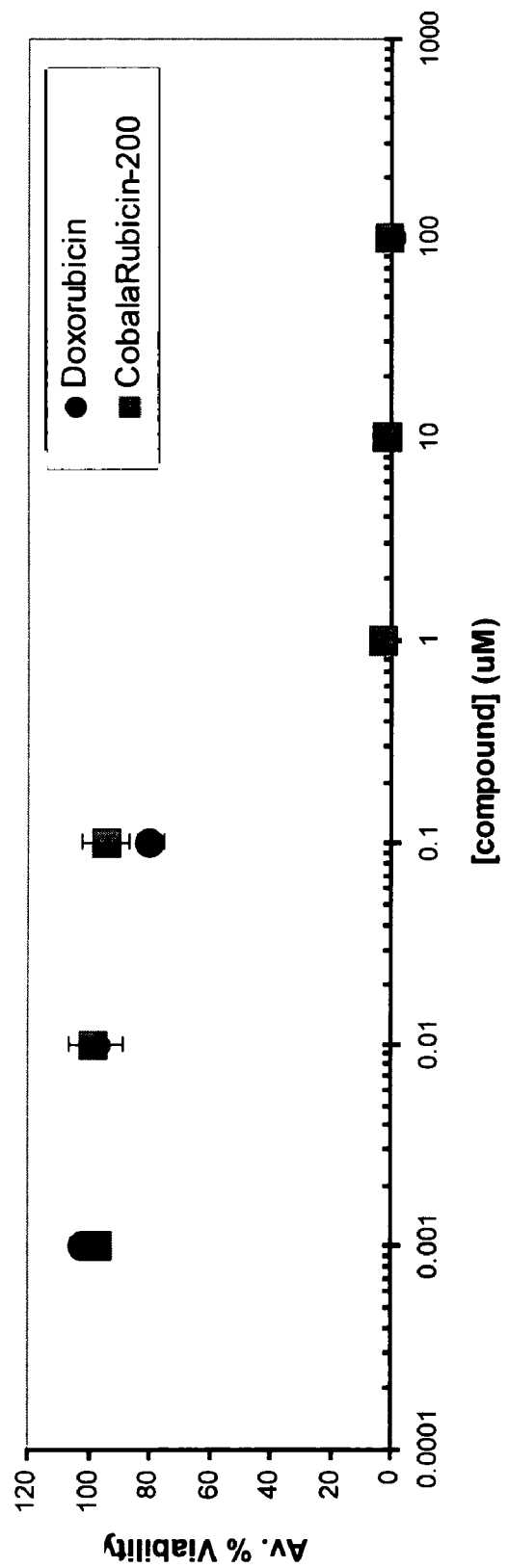
FIG. 6d depicts a chart of the in vitro comparison of free doxorubicin versus a doxorubicin-cobalamin conjugate (according to the invention) against SK-N-MC cells.

FIGS. 6a-6d depict the results of in vitro assays of the conjugate against four cell lines. FIG. 6A is a chart depicting the results of the conjugate against MCF-7 cells, cells derived from a human breast cancer cell line. FIG. 6B is a chart depicting the results of the conjugate against SK-BR-3 cells, cells derived from a human Caucasian breast adenocarcinoma cell line. FIG. 6C is a chart depicting the results of the conjugate against HL-60 cells, cells derived from a human promyelocytic leukemia cell line. FIG. 6D is a chart depicting the results of the conjugate against SK-N-MC cells, cells derived from a human brain neuroblastoma (neuroepithelioma) cell line. The assay employed is the CellTiter-Glo™ Luminescent Cell Viability Assay from Promega Corporation, which is recognized in the art as being predictive of the effect of a compound on cell viability. The assay is detailed in Examples 4-7. The method described by Promega Corporation (Technical Bulletin No. 288) was followed with no exceptions. The results suggest that CobalaRubicin 200 has the same effectiveness as doxorubicin and is slightly less potent than doxorubicin.

Figure 7:
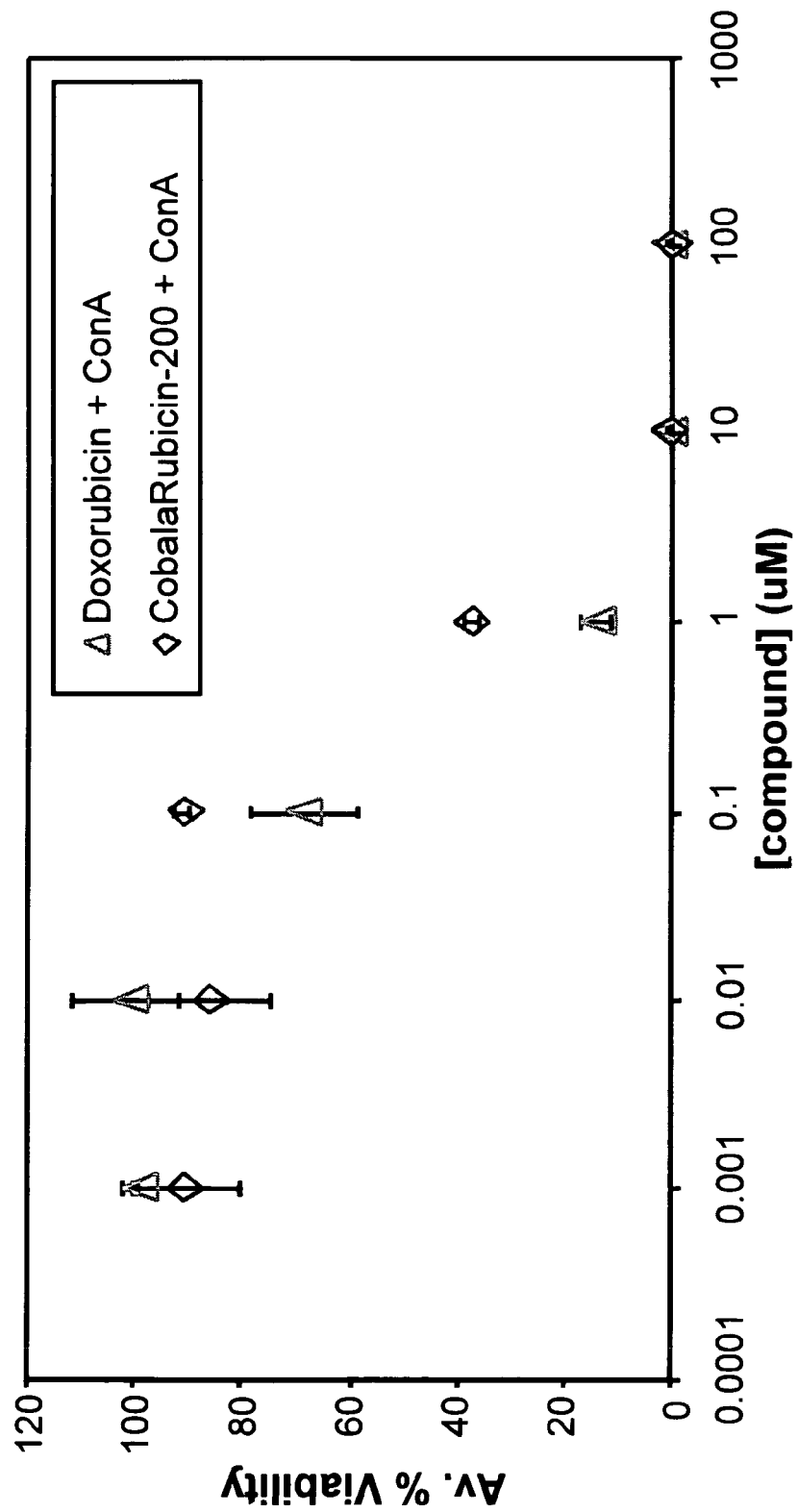
FIG. 7 depicts a chart of the in vitro comparison of free doxorubicin versus a doxorubicin-cobalamin conjugate against normal murine lymph node cells.

FIG. 7 is a chart depicting the results of an in vitro assay of the conjugate against normal murine lymph node cells. The assay employed is the CellTiter-Glo™ Luminescent Cell Viability Assay from Promega Corporation, which is recognized in the art as being predictive of the effect of a compound on cell viability. The assay is detailed in Example 8. The method described by Promega Corporation (Technical Bulletin No. 288) was followed with no exceptions. The results suggest that CobalaRubicin-200 is as effective as doxorubicin but shows slightly less potency than doxorubicin against normal cells.

Figure 8:
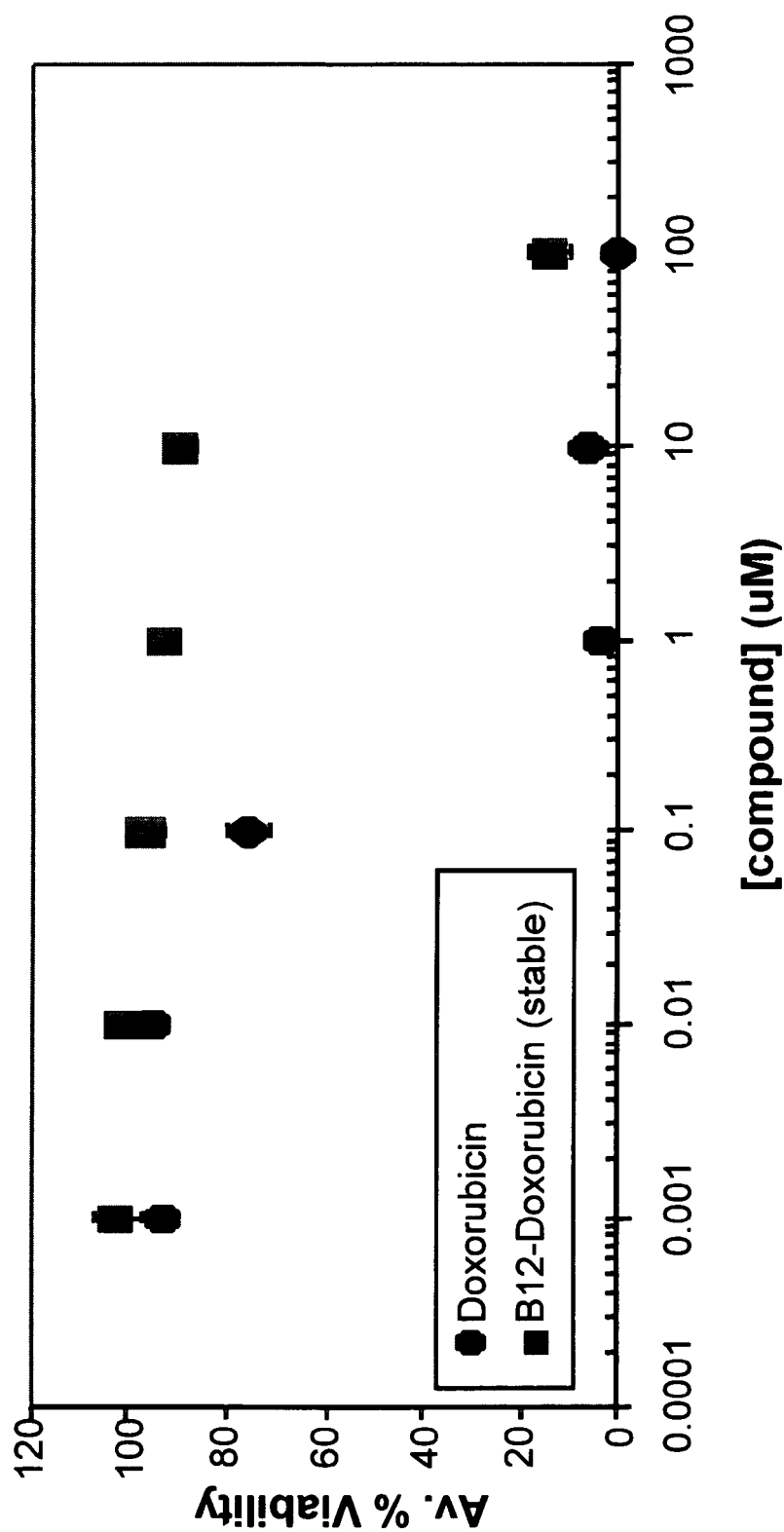
FIG. 8 depicts a chart of the in vitro comparison of free doxorubicin versus an "enzyme-10) cleavage stable" doxorubicin-cobalamin conjugate (not according to the invention) against SK-N-MC cells.

To test whether cleavage and release of doxorubicin is important for the activity of CobalaRubicin-200, the activity of B12-Doxorubicin (FIG. 1b; an "enzyme-cleavage stable" doxorubicin-cobalamin conjugate (not according to the invention)) was tested in the in vitro viability assay against SK-N-MC cells. FIG. 8 is a chart depicting the results of an in vitro assay of the stable conjugate against SK-N-MC cells, cells derived from a human brain neuroblastoma (neuroepithelioma) cell line. The assay employed is the CellTiter-Glo™ Luminescent Cell Viability Assay from Promega Corporation, which is recognized in the art as being predictive of the effect of a compound on cell viability. FIG. 8 depicts the results of the assay conducted according to Example 9. The method described by Promega Corporation (Technical Bulletin No. 288) was followed with no exceptions. B12-Doxorubicin (stable) is not cleavable by cathepsin and as a result a significant amount of the doxorubicin is not released intracellulary. The chart shows that the B12-doxorubicin conjugate that is not cleaved possesses little to no cytotoxicity or efficacy against SK-N-MC cells. In contrast, the conjugate (13) which possesses a cleavable linker is very efficacious against SK-N-MC cells (see FIG. 6d). The results indicate that for sufficient cytotoxic activity to exist, the linker must be cleaved to allow for release of doxorubicin from B12.

Efficacy of the conjugate (13) was also established in an in vivo animal model wherein athymic mice possessing an MX-1 human breast carcinoma xenograft were divided into three groups and treated with either free doxorubicin control, saline control and cobalarubicin. The in vivo study was conducted according to example 3. The comparison was based upon tumor size versus days after administration. The results depicted in FIG. 9 indicate that the conjugate possesses much greater efficacy than the free drug. At about 2-4 weeks after administration of a single does of the conjugate, a substantial decrease in tumor size was observed.

The present inventors have discovered that a conjugate according to the present invention possesses high efficacy (cytotoxicity) against tumor cell lines but provides reduced systemic toxicity to the host. The conjugate can be administered at a higher dose than the corresponding free anti-tumor drug on a molar basis. The conjugate (13) can be administered at a dose that is at least 2.3 time higher than that of free doxorubicin on a molar basis and still exhibit less systemic toxicity and an improved therapeutic benefit. When the free doxorubicin was administered at the same high molar dose as the doxorubicin conjugate, the mice were killed by the free doxorubicin but not by the doxorubicin conjugate. Accordingly, the invention provides a method of reducing the systemic toxicity of an anti-tumor drug by administering the anti-tumor drug as a 5'-OH conjugate of cobalamin, wherein the cobalamin-5'-O-anti-tumor drug conjugate exhibits reduced systemic toxicity to a subject as compared to the unconjugated anti-tumor drug on a molar basis. The invention also provides a method of increasing the maximum tolerated dose of an anti-tumor drug comprising the step of administering the anti-tumor drug as a 5'-OH conjugate of cobalamin, wherein the cobalamin-5'-O-anti-tumor drug conjugate exhibits reduced systemic toxicity to a subject as compared to the unconjugated anti-tumor drug on a molar basis, and the maximum tolerated dose of the conjugate is higher than the maximum tolerated dose of the unconjugated anti-tumor drug on a molar basis.

Figure 10:
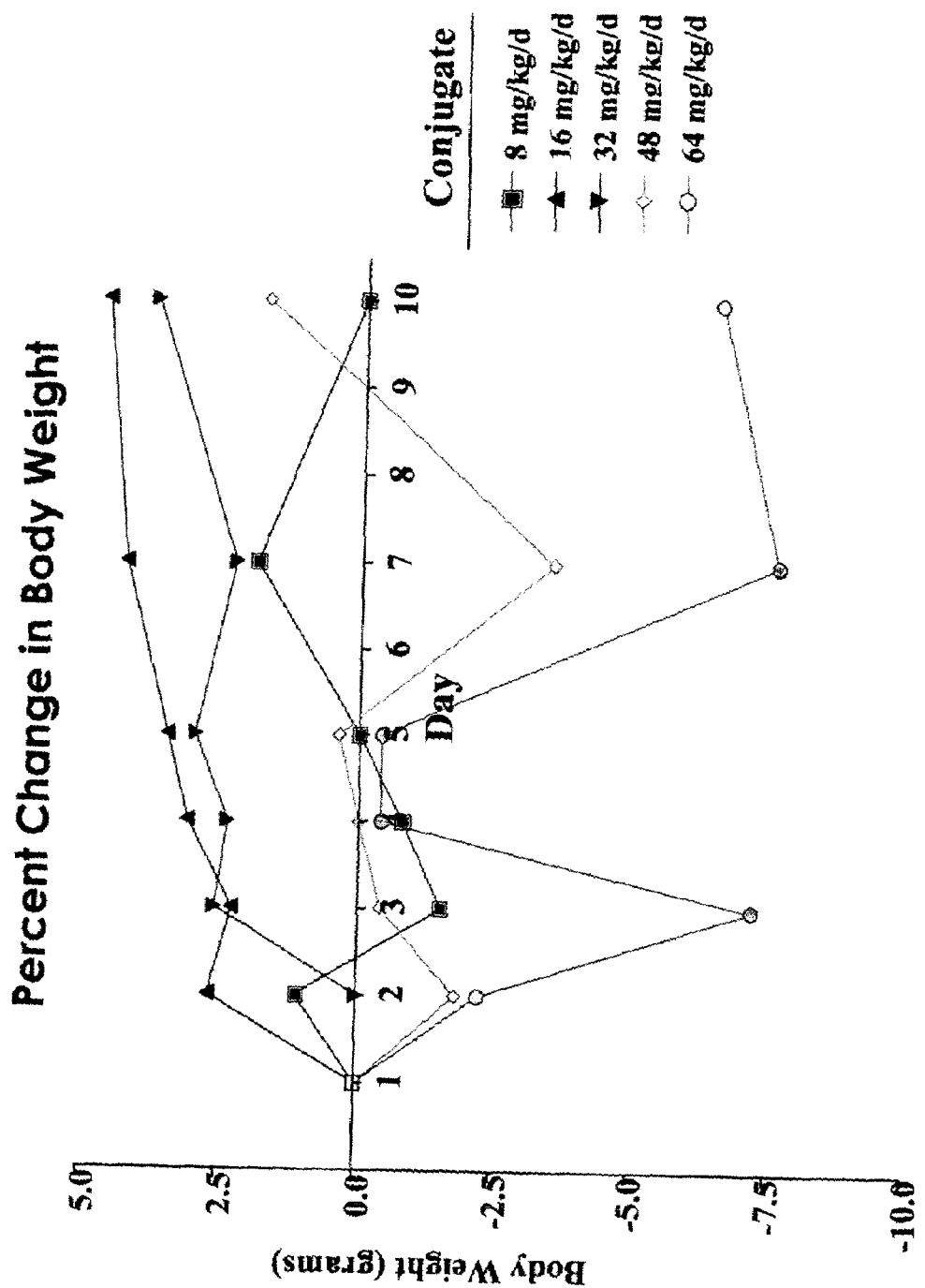
FIG. 10 depicts a chart summarizing the percent change in body weight of mice treated according to Example 10 with differing doses of the conjugate (13). The percent change in body weight was determined daily and the conjugate was administered daily at the indicated doses.

FIG. 10 depicts a chart of the results of a study to determine the maximum tolerated dose (MTD) of the conjugate (13) in mice according to the procedure of Example 10. The conjugate was administered at a dose of 6, 12, 32, 48 or 64 mg per kg of body weight per day (mg/kg/d). The results, depicted in FIG. 10, showed a somewhat erratic pattern but a clear trend of increasing toxicity with increasing dose, as measured by percent mean body weight loss. The data suggest that the conjugate was well tolerated at a dose of up to about 48 mg/kg/d. In a separate study, it was determined that the MTD for unconjugated doxorubicin was at least 2.3 times lower than for the conjugate on a molar basis.

Figure 11:
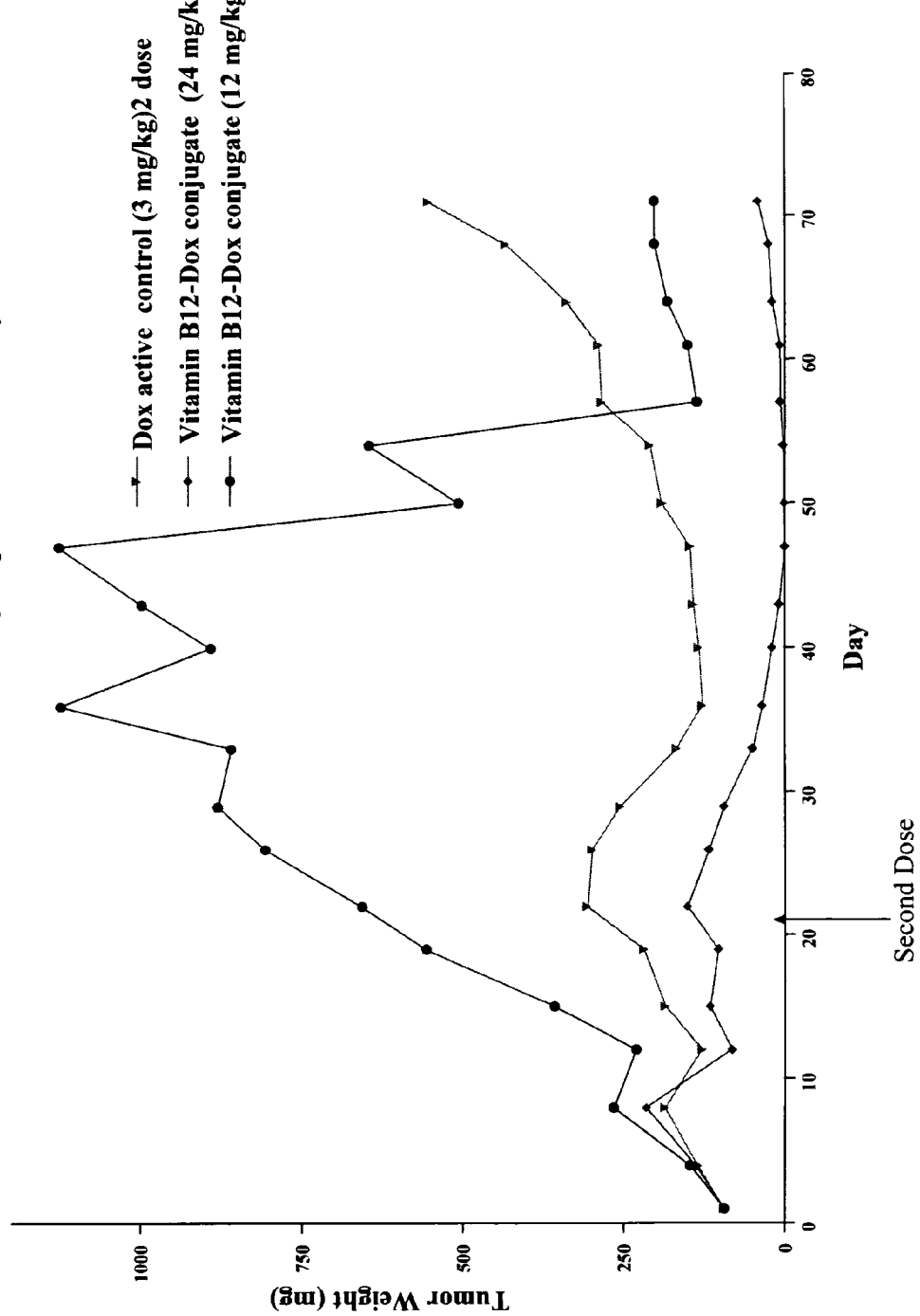
FIG. 11 depicts a chart of the in vivo comparison of free doxorubicin control and cobalamin-doxorubicin conjugate in terms of tumor size versus days after administration in mice treated according to the procedure of Example 11.

A study was conducted according to Example 11 to determine the tumor growth delay and tumor size reduction effects of the conjugate and free anti-tumor drug against MX-1 human breast cancer xenograft in athymic mice, wherein the conjugate and doxorubicin were administered in two cycles. The results of this study at study day 71 are shown in FIG. 11. The results indicate that a two-cycle treatment with the conjugate was extremely effective at reducing tumor size and delaying tumor growth. The no treatment group showed a median time to endpoint of 27.1 days, significantly less days than the treatment group, with no members developing partial regression, complete regression or long term tumor free survival. Body weight changes were not significant and there were no treatment or non-treatment related deaths. The 2-cycle, 3 mg/kg/day, of doxorubicin treatment group responded to treatment showing time to endpoint of at least 44 days longer than control mice. At 71 days, 1 in 10 mice in this group developed complete regression and a significant percentage of these were long-term, tumor-free survivors. Maximum body weight loss was 15% with no treatment or nontreatment related deaths. Two cycles of 24 mg/kg/day treatment with the bioconjugate was associated with a time to endpoint of 44 days longer than control mice. At 71 days 9 of 10 mice in this group developed complete regression and 7 of 10 were long-term, tumor-free survivors. Maximum body weight loss was 10% with no treatment or nontreatment related deaths.

The conjugate was also administered at a lower dose than above and a delay in tumor growth was observed over non-treatment control, but the conjugate was less efficacious than free doxorubicin on a molar equivalent basis (data not shown).

Figure 12A:
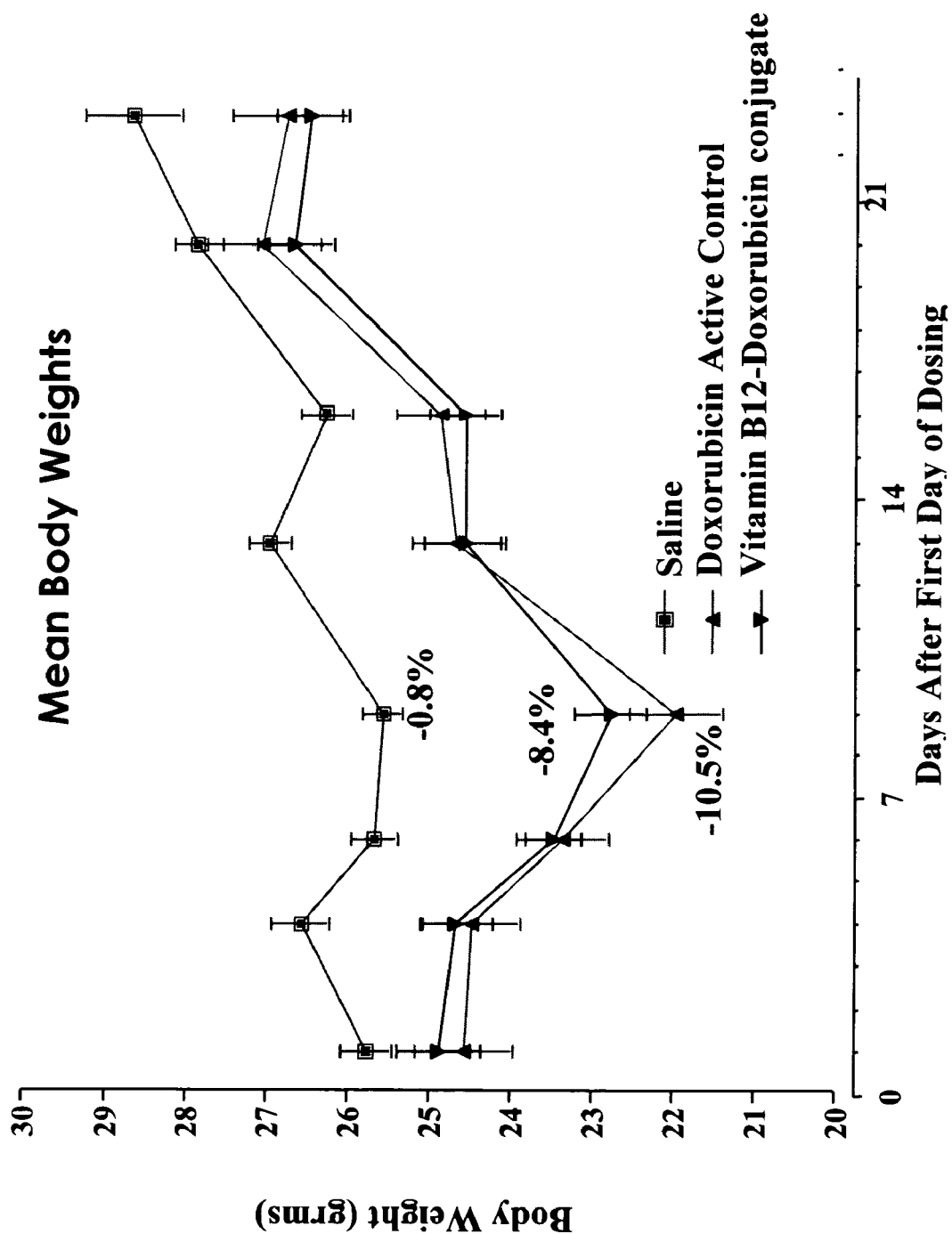
FIG. 12a depicts a chart of the in vivo comparison of saline control, free doxorubicin control and cobalamin-doxorubicin conjugate in terms of mean body weight versus days after administration in mice treated according to the procedure of Example 12.
Figure 12B:
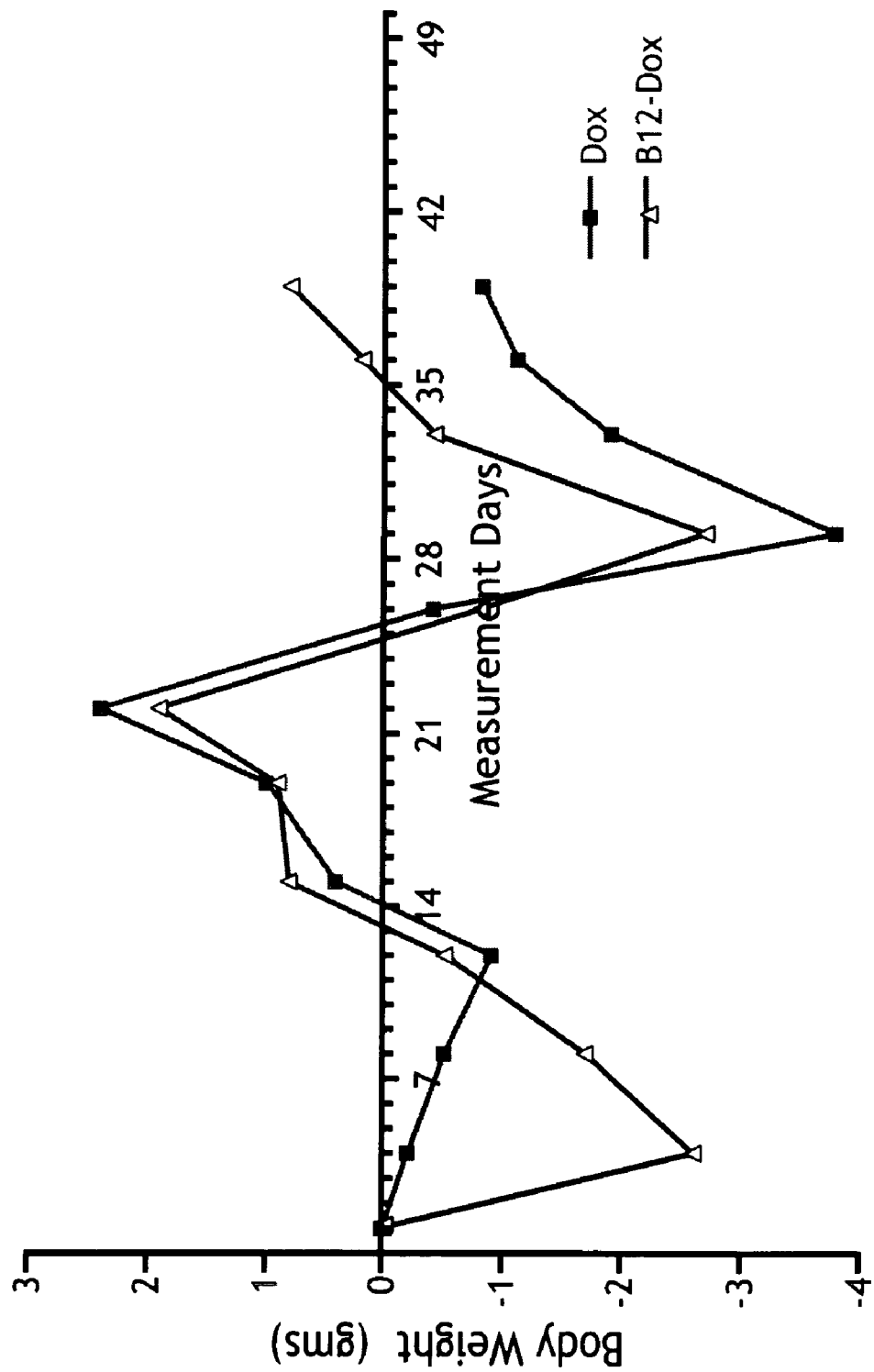
FIG. 12b depicts a chart of the in vivo comparison of free doxorubicin control and cobalamin-doxorubicin conjugate in terms of body weight changes versus days after administration in mice treated according to the procedure of Example 12.

Data from the single-cycle study (Example 3) was tabulated and is depicted in abbreviated form in FIG. 12a. Similarly, data from the two-cycle study (example 11) was tabulated and depicted in abbreviated form in FIG. 12b. While administration of doxorubicin in any form caused a significant change in body weight loss compared to control animals, the increase amount of doxorubicin in the conjugate (2.3-fold increase) was not associated with additional toxicity. The study described in example 11 illustrates the dramatic effect of two-cycles of doxorubicin on body weight. Treatment with either doxorubicin or the bioconjugate caused significant weight loss. However, animals treated with the conjugate tended recover from their weight loss sooner than the group given native doxorubicin, even though the equivalent dose of doxorubicin in the conjugate was 2-fold greater. The results indicate that the performance of the conjugate (13) tracks that of free doxorubicin in the doses administered even though the conjugate was administered at a dose more than 2 times (or about 2.3 times) the dose of native (unconjugated, free) doxorubicin.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

As used herein, "pharmaceutically acceptable salts" refer to derivatives of the disclosed compounds wherein the therapeutic compound is modified by making acid or base salts thereof.

Examples of pharmaceutically acceptable salts include, but are not limited to, mineral or organic acid salts of the pharmaceutically active agent. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and other known to those of ordinary skill in the pharmaceutical sciences. Lists of suitable salts are found in texts such as *Remington's Pharmaceutical Sciences,* 18th Ed. (Alfonso R. Gennaro, ed.; Mack Publishing Company, Easton, Pa., 1990); *Remington: the Science and Practice of Pharmacy* 19$^{th}$ Ed. (Lippincott, Williams & Wilkins, 1995); *Handbook of Pharmaceutical Excipients*, 3$^{rd}$ Ed. (Arthur H. Kibbe, ed.; Amer. Pharmaceutical Assoc., 1999); the *Pharmaceutical Codex: Principles and Practice of Pharmaceutics* 12$^{th}$ Ed. (Walter Lund ed.; Pharmaceutical Press, London, 1994); The United States Pharmacopeia: The National Formulary (United States Pharmacopeial Convention); and *Goodman and Gilman's: the Pharmacological Basis of Therapeutics* (Louis S. Goodman and Lee E. Limbird, eds.; McGraw Hill, 1992), the disclosures of which are hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. An anti-tumor, or anticancer, drug is inherently cytotoxic to tumor or cancer cells. However, a composition or dosage containing such a drug is still considered pharmaceutically acceptable as long as it provides the intended therapeutic benefit without undue systemic toxicity to a subject to whom it is administered. The acceptable level of systemic toxicity will be determined according to known principles in the field of tumor and cancer therapy.

By the term "effective amount", it is understood that, with respect to, for example, pharmaceuticals, a therapeutically effective amount is contemplated. A therapeutically effective amount is the amount or quantity of conjugate or anti-tumor drug that is sufficient to elicit the required or desired therapeutic response, or in other words, the amount that is sufficient to elicit an appreciable desired clinical response when administered to a patient.

The following examples should not be considered exhaustive, but merely illustrative of only a few of the many embodiments contemplated by the present invention. The methods described herein can be followed to prepare conjugates according to the invention.

A Waters HPLC system including a Delta 600 pump with model 600 controller and a 2996 PDA detector was used for both analytical and preparative work. 0.1% acetic acid in water and acetonitrile were used as aqueous and organic buffers, respectively. A Waters Delta-Pak $C_{18}$ 15 μm 100 Å 3.9×300 mm column (P/N WAT011797) and 1 mL/min flow rate were used for analytical work; a Waters Delta-Pak Radial Compression $C_{18}$ 15 μm 100 Å 25×100 mm column (P/N WAT011797) and 20 mL/min flow rate were used for preparative work. Mass spectra were acquired on an Applied Biosystems API 2000 electrospray mass spectrometer in positive ion mode.

EXAMPLE 1

The following procedure was used to prepare the exemplary doxorubicin-VB conjugate of FIG. 1.

Step 1. Fmoc-Lys(MMT) (1)

To a stirred suspension of Fmoc-Lys (5.1067 g, 13.8618 mmol, 1.0 eq) in methylene chloride (75 ml) at room temperature was added trimethylsilyl chloride (3.8 ml, 29.7312 mmol, 2.14 eq). The mixture was refluxed at 50° C. for 1 hr and the appearance of the solid in the reaction mixture changed. After being cooled in an ice bath, DIEA (7.5 ml, 43.0561 mmol, 3.11 eq) was added, the mixture became homogeneous, and followed by p-anisyldiphenylmethyl chloride (4.4955 g, 14.5580 mmol, 1.05 eq). The orange-red solution was stirred at room temperature overnight (20 hrs). After removal of solvent, the residue was partitioned between ethyl acetate (200 ml) and pH5 buffer (0.05M phthalic acid, adjusted with 10N KOH to pH 5.0). The organic phase was washed with more pH5 buffer (50 ml×2), water (50 ml×1), brine (50 ml×2), dried over magnesium sulfate. After removal of solvent and being dried in vacuo, 9.7336 g of pale yellow foam was obtained.

Step 2. Lys(MMT) (2)

To a stirred solution of Fmoc-Lys(MMT) (9.7336 g) in 100 ml of mixture of methylene chloride and acetonitrile (1:1) at room temperature was added diethylamine (100 ml). The mixture was stirred at room temperature for 1.5 hrs. After removal of solvent, the residue was flushed with acetonitrile at 60° C. (90 ml×2), washed with acetonitrile (20 ml×3) and ether (20 ml×3). The solid was then dissolved as far as possible in 1:1 $CH_2Cl_2/CH_3OH$ (200 ml) and some solid byproduct was removed by filtering through filter paper. After removal of solvent and being dried in vacuo, 4.7707 g (82.2%, based on Fmoc-Lys) of pale yellow foam was obtained. ES(+)-MS: 147(Lys+1), 273(MMT).

Step 3. Fmoc-Phe-OSu (3)

To a suspension of Fmoc-Phe (1.9442 g, 5.0186 mmol, 1.0 eq) and N-hydroxysuccinimide (0.6095 g, 5.2959 mmol, 1.06 eq) in methylene chloride (50 ml) cooled in an ice bath, was added DCC (1.0880 g, 5.2731 mmol, 1.05 eq). The mixture was stirred at room temperature overnight. The resulting DCU was removed by filtration and the filtrate was condensed and dried in vacuo to give 2.7664 g of white foam.

Step. 4. Fmoc-Phe-Lys(MMT) (4)

To a stirred suspension of Fmoc-Phe-OSu (2.0702 g, 4.2728 mmol, 1.0 eq) and Lys(MMT) (1.7995 g, 4.2995 mmol, 1.01 eq) in DMF (30 ml) was added DIEA (1.5 ml, 8.6112 mmol, 2.02 eq). The solid dissolved gradually and the solution was stirred at room temperature overnight. The reaction mixture was partitioned between ethyl acetate (100 ml) and pH5 buffer (0.05M phthalic acid, adjusted with 10N KOH to pH 5.0, 200 ml). The aqueous solution was extracted with more ethyl acetate (50 ml×2). The combined organic phase was washed with brine (50 ml×3), dried over $MgSO_4$. After removal of solvent and being dried in vacuo, 3.3014 g (98.1%) of pale-yellow foam was obtained. ES(+)-MS: 516(M-MMT+1), 273(MMT).

Step 5. Fmoc-Phe-Lys(MMT)-PABOH (5)

To a stirred solution of Fmoc-Phe-Lys(MMT) (3.3014 g, 4.1898 mmol, 1.0 eq) and 4-aminobenzyl alcohol (0.6219 g, 5.0495 mmol, 1.21 eq) in methylene chloride (20 ml) was added 2-ethoxy-1-ethoxycarbonyl-1,2-dihydroquinoline (1.5589 g, 6.3037 mmol, 1.50 eq). The mixture was stirred at room temperature overnight. After removal of solvent, the residue was triturated with ether (50 ml). The mixture was left to stand at room temperature for 2 hours and the resulting solid was collected, washed with ether (15 ml×3), dried in vacuo. 2.1071 g (56.3%) of white solid were obtained. The ether filtrate was condensed. The residue was suspended in benzene (10 ml) and precipitated with hexane (10 ml). This process was repeated two more times. The resulting solid was collected, washed with benzene/hexane (1:1, 10 ml×3), dried in vacuo. Another 0.8864 g (23.7%) of white solid was obtained. Total yield: 80.0%. ES(+)-MS: 893(M), 915(M+Na), 810(M-PABOH+Na), 273(MMT).

Step 6. Fmoc-Phe-Lys(MMT)-PABC-PNP (6)

To a stirred solution of Fmoc-Phe-Lys(MMT)-PABOH (1.1182 g, 1.2520 mmol, 1.0 eq) and bis(4-nitrophenyl) carbonate (1.9102 g, 6.2792 mmol, 5.02 eq) in methylene chloride (50 ml) was added DIEA (0.65 ml, 3.7315 mmol, 2.98 eq). The yellow solution was stirred at room temperature overnight. After removal of solvent, the residue was dissolved in ethyl acetate (150 ml), washed with the pH 5 buffer (0.05M phthalic acid, adjusted with 10N KOH to pH 5.0) (100 ml×1, 50 ml×1), brine (50 ml×2), dried over $MgSO_4$. After removal of solvent, the residue was purified by silica column (2.4×20 cm), eluting with $CH_2Cl_2$/ether (9:1-8:2), giving 0.8027 g (60.6%) of pale-yellow foam. ES(+)-MS: 1058(M), 786(M-MMT), 273(MMT).

Step 7. Fmoc-Phe-Lys(MMT)-PABC-Dox (7)

To a stirred solution of Fmoc-Phe-Lys(MMT)-PABC-PNP (0.6414 g, 0.6061 mmol, 1.0 eq) and doxorubicin hydrochloride (0.3465 g, 0.5974 mmol, 1.0 eq) in N-methylpyrrolindinone (15 ml) was added DIEA (0.12 ml, 0.6889 mmol, 1.15 eq). The red solution was stirred in the dark (wrapped with aluminum foil) at room temperature overnight. The reaction mixture was diluted with ethyl acetate (150 ml), washed with water (100 ml×1, 50 ml×2), brine (50 ml×1), dried over $MgSO_4$. After removal of solvent, the residue was purified by silica column (2.4×19 cm), eluting with 5% methanol in methylene chloride, giving 0.8700 g (99.6%) of red glassy solid.

Step 8. Ph-Lys(MMT)-PABC-Dox (8)

To a stirred suspension of Fmoc-Phe-Lys(MMT)-PABC-Dox (0.6472 g) in methylene chloride (50 ml) was added diethylamine (12.5 ml). The mixture turned deep brown and the solid dissolved. It was stirred at room temperature for 3 hours. After removal of solvent, the residue was dissolved in methylene chloride (4 ml) and added to a stirred ether solution (100 ml). The resulting precipitate was collected, washed with ether (10 ml×3), dried in vacuo, giving 0.5292 g (96.4%) of orange-red solid. ES(+)-MS: 1241.2(M+1), 968.8(M-MMT+1).

Step 9. $B_{12}$-5'-OCO-(1,2,4-triazole) (9)

To a stirred solution of cyanocobalamin (2.0380 g, 1.5036 mmol, 1.0 eq) in DMSO (30 ml) was added 1,1'-carbonyldi (1,2,4-triazole) (0.3759 g, 2.2903 mmol, 1.52 eq). The mixture was stirred at room temperature for 30 min and then added to a stirred mixture of $CH_2Cl_2$/ether (1:1, 200 ml). The resulting precipitate was collected, washed with acetone (50 ml×3) and ether (50 ml×1), dried in vacuo, giving 2.3706 g of red powder.

Step 10. $B_{12}$-5'-OCONH$(CH_2)_5$COOH (10)

The above intermediate 9 was added to a stirred suspension of 6-aminohexanoic acid (0.2180 g, 1.6620 mmol, 1.11 eq) and DIEA (0.54 ml, 3.100 mmol, 2.06 eq) in DMSO (30 ml). The mixture was stirred at room temperature overnight. The reaction mixture was filtered through glass wool to get rid of unreacted 6-aminohexanoic acid. The filtrate was added to a stirred mixture of $CH_2Cl_2$/ether (1:1, 200 ml). The resulting precipitate was collected, washed with acetone (50 ml×3) and ether (50 ml×1), dried in vacuo, giving 2.3562 g of red powder. It was purified by silica column, eluting with water, giving 1.3546 g (59.6%) of red powder. ES(+)-MS: 1513.8(M+1).

Step 11. $B_2$-5'-OCONH$(CH_2)_5$COOSu (11)

To a stirred solution of compound 10 (0.5706 g, 0.3772 mmol, 1.0 eq) and N-hydroxysuccinimide (0.2789 g, 2.4233 mmol, 6.42 eq) in DMSO (10 ml) was added diisopropylcarbodiimide (1.0 ml, 6.3867 mmol, 16.93 eq). The mixture was stirred at room temperature overnight. The reaction mixture was added to 100 ml of stirred ether/$CH_2Cl_2$ (1:1). The resulting precipitate was collected, washed with acetone (10 ml×2), ether (10 ml×2), dried in vacuo. 0.6314 g of red powder was obtained. ES(+)-MS: 1610.7(M+1).

Step 12. $B_{12}$-5'-OCONH$(CH_2)_5$CO-Phe-Lys(MMT)-PABC-Dox (12)

A solution of compound 8 (0.5400 g, 0.4353 mmol, 1.0 eq) and compound 11 (0.8491 g, 0.5275 mmol, 1.21 eq) in DMSO (10 ml) was stirred at room temperature for one hour. Then the reaction mixture was added to 100 ml of stirred ether/$CH_2Cl_2$ (1:1), the resulting precipitate was collected, washed with acetone (15 ml×2), methylene chloride (15 ml×2) and ether (15 ml×2), dried in vacuo. 1.1040 g (92.7%) of red powder were obtained. ES(+)-MS: 1368.3[(M+1)/2].

Step 13. $B_{12}$-5'-OCONH$(CH_2)_5$CO-Phe-Lys-PABC-Dox (13)

To a stirred suspension of compound 12 (0.5715 g, 0.2090 mmol, 1.0 eq) in methanol (15 ml), water (15 ml) and methylene chloride (15 ml), was added anisole (2.4 ml, 21.9715 mmol, 105.1 eq) and dichloroacetic acid (1.8 ml, 21.9035 mmol, 104.9 eq). The mixture was stirred at room temperature for 2 hours. HPLC indicated most of the starting material consumed. The organic solvents were removed with rotary evaporator. The residue was diluted with water (50 ml). The aqueous phase was poured into a separatory funnel. The sticky solid was rinsed with ether (25 ml×3), dissolved in methanol (4 ml), added to stirred ether (100 ml). The resulting precipitate was collected, washed with ether (10 ml×3), dried in vacuo, giving 0.2353 g of red powder. The aqueous phase was extracted with ether (25 ml×3). The organic solvent dissolved in aqueous solution was removed with rotary evaporator. Then the aqueous solution was centrifuged and desalted with Waters Sep-Pak tC18 cartridge (P/N WAT036810). Another portion (0.262 g) of crude product was obtained. The crude product was purified by HPLC, giving 85.6 mg (16.6%) of red powder. ES(+)-MS: 1232.3[(M+1)/2].

EXAMPLE 2

The following method was used to confirm the cleavability of the anti-tumor conjugates, esp. (13), by cathepsin B. A conjugate stock solution (5% DMSO in water) containing the doxorubicin-CB conjugate (13) (1.0 mM) was prepared. Cathepsin B (human liver; Calbiochem, #219364; MW: 27500; specific activity: 274 units/mg protein, 5 units) was placed in 32.1 µl of NaOAc (20 mM, 1 mM EDTA, pH 5.0). Then 1 µL of cathepsin B was activated with 4 µL of 30 mM DTT/15 mM EDTA at room temperature for 15 min. This solution was diluted with 665 µL of 25 mM NaOAc/1 mM EDTA buffer (pH5.0, pre-incubated at 37° C.) to prepare an enzyme stock solution. 96 µL of the enzyme stock solution was mixed with 1 µL of conjugate stock solution, and incubated at 37° C. for 60 min. Final concentration: [cathepsin B]=30 nM, [substrate]=10 µM. The extent of reaction was monitored by periodic sampling and subsequent HPLC analysis (buffer A: 0.1% HOAc, buffer B: acetonitrile, 20-50% B over 20 min, monitored at 495 nm, Tr=7.2 min for B12-Phe-Lys, Tr=15.8 min for doxorubicin and Tr=18.8 min for substrate). Typical results indicated that 83% of the conjugate was cleaved during a period of 60 min.

A similar procedure can be used to evaluate the cleavability of a conjugate according to the invention by cathepsin B. In order to evaluate the cleavability by other intracellular enzymes, assays as described in texts such as the series of books entitled *Methods in Enzmology*, can be followed, with the exception that the conjugate of the invention will be substituted for the native substrate of any particular enzyme. Confirmation of cleavage of the conjugate by that enzyme is sufficient to warrant conducting further in vitro and/or in vivo evaluation of the conjugate for treatment of tumors.

EXAMPLE 3

Figure 9:
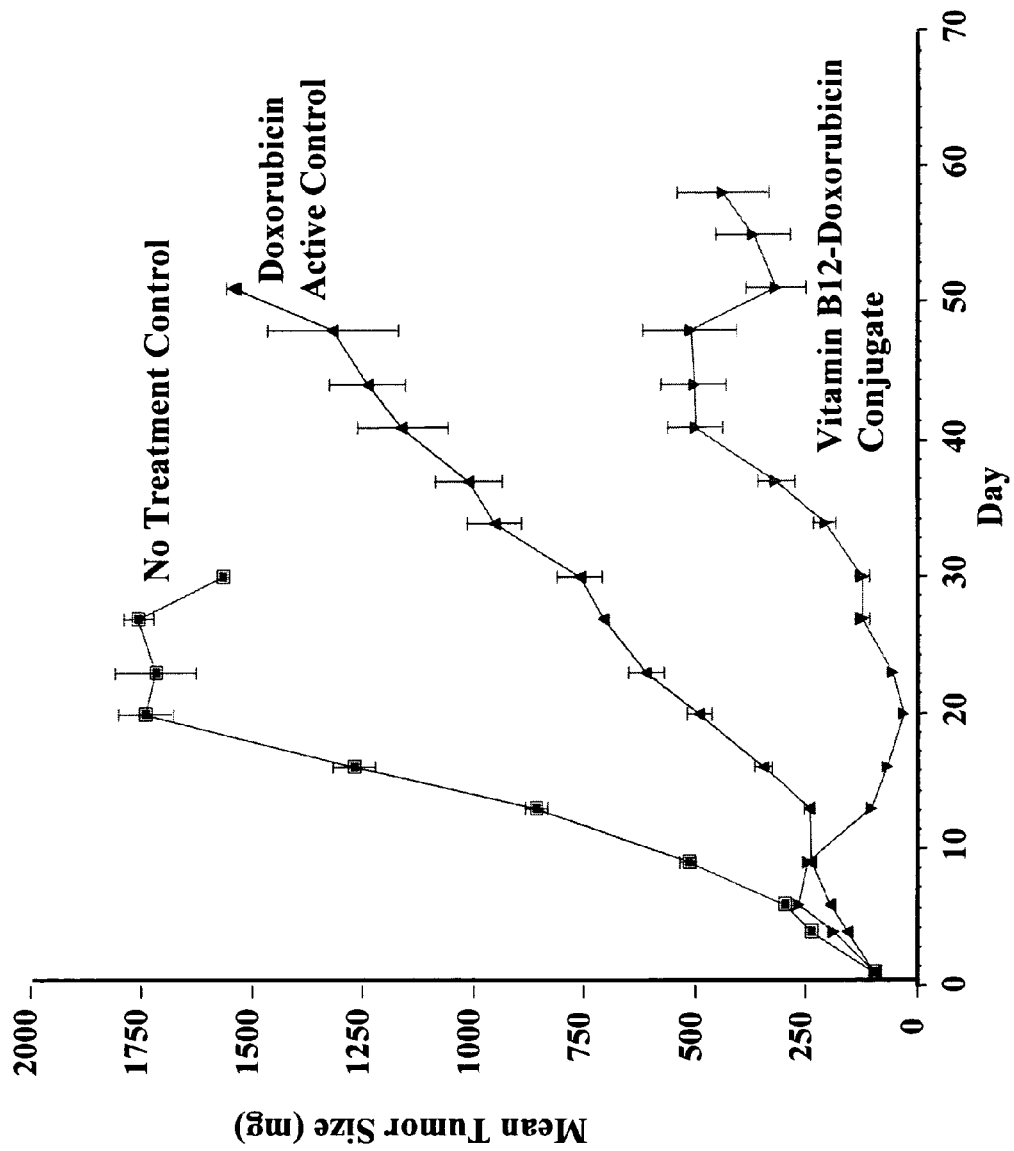
FIG. 9 depicts a chart of the in vivo comparison of free doxorubicin control, saline control and cobalarubicin (a doxorubicin-cobalamin conjugate) in athymic mice possessing an MX-1 human breast carcinoma xenograft. The comparison is based upon tumor size versus days after administration.

The following procedure was used to investigate the affect of the cobalamin-doxorubicin conjugate on tumor growth, particularly for the delay of growth of MX-1 human breast carcinoma xenograft in athymic mice. Female nude Harlan mice are implanted subcutaneously with 1 mm$^3$ MX1 solid tumor fragments in the flank. During the pre-dose phase of implantation and growth, tumors are initially monitored twice weekly, and then daily as the neoplasms approach the desired size of 80-120 mg. When the majority of tumors have attained the targeted weight range (80-120 mg), mice are pair-matched into 4 treatment groups of 10 mice each comprised of no treatment, 3 mg/kg/day×5 days intravenous Doxorubicin (active control), 64 mg/kg/day×5 days intravenous bioconjugate and 32 mg/kg/day×5 days intravenous bioconjugate. Test articles were administered on the day of pair matching, Day 1. The tumor growth delay endpoint is reached when the tumor on the mouse reaches 1.5 gm weight, estimated by the formula: Tumor weight (mg)=$w^2 \times l/2 \times 1$ mg/mm$^3$, where w=width (mm) and l=length (mm) of the tumor. The median time to endpoint is calculated for each treatment group. The results of this study are shown in FIG. 9. The no treatment group showed a median time to endpoint of 17.8 days, with no members developing partial regression, complete regression or long term tumor free survival. Body weight changes were negligible and there were no treatment or non-treatment related deaths. Treatment with Doxorubicin (active control, 3 mg/kg/day) caused a median delay in tumor growth of 39.5 days, an increase of 21.7 days over control (122%). There were no partial or complete tumor regressions and no long-term, tumor-free survivors. The mean body weight loss was observed on day 9 at −10.5% with no other treatment or nontreatment related deaths. The 64 mg/kg/day treatment group developed severe toxicity and were terminated on Day 4. The 32 mg/kg/day treatment group responded to treatment showing median time to endpoint of 62.1 days, 44.3 days longer than control and 22.6 days longer than the Doxorubicin active control. Over the course of the study, 6 mice in this group developed complete regression and 4 were long-term, tumor-free survivors. Maximum body weight loss was observed on day 9 at −8.4% with no treatment or nontreatment related deaths.

EXAMPLE 4

The following procedure was used for the in vitro evaluation of the doxorubicin-cobalamin conjugate against MCF-7 cells. The results are detailed in FIG. 6a The MCF-7 cell line was obtained from ATCC and incubated at 37° C. with 5% $CO_2$. MCF-7 cells were maintained in Dulbecco's Modified Eagle Medium (D-MEM) with GlutaMAX, with high glucose, with pyridoxine hydrochloride, without sodium pyruvate (Gibco) and supplemented with 10% heat inactivated defined fetal bovine serum (HyClone), penicillin-streptomycin (Gibco) to a final concentration of 10 units penicillin and 10 µg streptomycin per ml and an additional 2 mM L-glutamine (Gibco). For the viability assays, cells were plated in 96-well plates in 100 µl of medium. MCF-7 cells were seeded at an initial density of 5000 cells per well.

Doxorubicin and CobalaRubicin-200 stocks and stock solutions, prepared in 5% DMSO in water, were stored at −20° C. and protected from light. Each compound was tested at six final concentrations covering ten-fold dilutions from 100 µM down to 10 nM. 10× stock solutions were made and 10 µl added to each of three wells containing cells. Compounds were added approximately 24 hours after the cells were plated. Untreated control cells received 10 µl of 5% DMSO. Three wells containing medium alone were also included as a background control. The plates were placed back in the 37° C. incubator.

After 96 hours, the effects of doxorubicin and B12-S-doxorubicin on cell viability were determined using an assay from Promega. The CellTiter-Glo™ Luminescent Cell Viability Assay quantitates the ATP present in a culture, which correlates with metabolically active cells. Luminescence, which is dependent on ATP concentration, was measured for each individual well on a Wallac MicroBeta® JET Liquid Scintillation and Luminescence Counter. The average luminescence value of the three wells containing medium alone was subtracted from the raw data values to give corrected values. To correct for the background imparted by the red color of high concentrations of doxorubicin and B12-S-dox, the subtracted background value for cells treated with 10 or 100 µM was the luminescence of medium including 10 or 100 µM of doxorubicin or B12-S-dox, instead of just medium alone. The three corrected values for wells dosed with the same concentration of compound were averaged and the standard deviation calculated. Percent cell viability was calculated by considering the untreated cells as 100% viable. The corrected luminescence value was divided by the average corrected luminescence of untreated cells and multiplied by 100 to give the percent cell viability. Average percent cell viability of the triplicate wells and the standard deviation were calculated. This data was plotted as average percent cell viability (Av. % Viability) versus concentration of compound.

EXAMPLE 5

The following procedure was used for the in vitro evaluation of the doxorubicin-cobalamin conjugate against SK-BR-3 cells. The results are depicted in FIG. 6b. The SK-BR-3 cell line was obtained from ATCC and incubated at 37° C. with 5% $CO_2$. SK-BR-3 cells were maintained in Dulbecco's Modified Eagle Medium (D-MEM) with GlutaMAX, with high glucose, with pyridoxine hydrochloride, without sodium pyruvate (Gibco) and supplemented with 10% heat inactivated defined fetal bovine serum (HyClone), penicillin-streptomycin (Gibco) to a final concentration of 10 units penicillin and 10 µg streptomycin per ml and an additional 2 mM L-glutamine (Gibco). For the viability assays, cells were plated in 96-well plates in 100 µl of medium. SK-BR-3 cells were seeded at an initial density of 10000 cells per well. The viability assay and subsequent calculation were performed as described in EXAMPLE 4.

EXAMPLE 6

The following procedure was used for the in vitro evaluation of the doxorubicin-cobalamin conjugate against HL-60 cells. The results are depicted in FIG. 6c. The HL-60 cell line was obtained from ATCC and incubated at 37° C. with 5% $CO_2$. HL-60 cells were maintained in RPMI Medium 1640 with GlutaMAX (Gibco) supplemented with 10% heat inactivated defined fetal bovine serum (HyClone) and penicillin-streptomycin (Gibco). For the viability assays, cells were plated in 96-well plates in 100 µl of medium. HL-60 cells were seeded at an initial density of 5000 cells per well. The viability assay and subsequent calculation were performed as described in EXAMPLE 4.

EXAMPLE 7

The following procedure was used for the in vitro evaluation of the doxorubicin-cobalamin conjugate against SK-N-MC cells. The results are depicted in FIG. 6d. The SK-N-MC cell line was obtained from ATCC and incubated at 37° C. with 5% $CO_2$. SK-N-MC cells were maintained in Minimum Essential Medium (MEM) with Earle's salts, with L-glutamine (Gibco) and supplemented with 10% heat inactivated defined fetal bovine serum (HyClone), penicillin-streptomycin (Gibco) to a final concentration of 10 units penicillin and 10 µg streptomycin per ml and an additional 2 mM L-glutamine (Gibco). For the viability assays, cells were plated in 96-well plates in 100 µl of medium. SK-N-MC cells were seeded at an initial density of 20000 cells per well. The viability assay and subsequent calculation were performed as described in EXAMPLE 4.

EXAMPLE 8

The following procedure was used for the in vitro evaluation of the doxorubicin-cobalamin conjugate against normal murine lymph node cells. Lymphocytes were incubated at 37° C. with 5% $CO_2$ and maintained in RPMI Medium 1640 with GlutaMAX (Gibco) supplemented with 10% heat inactivated defined fetal bovine serum (HyClone) and penicillin-streptomycin (Gibco). For the viability assays, were plated in 96-well plates in 100 µl of medium. Cells were seeded at an initial density of $1.5 \times 10^5$ cells per well. The viability assay and subsequent calculation were performed as described in EXAMPLE 4.

EXAMPLE 9

The following procedure was used for the in vitro evaluation of the cathepsin cleavage stable doxorubicin-cobalamin conjugate against SK-N-MC cells. The results are depicted in FIG. 8. The SK-N-MC cell line was obtained from ATCC and incubated at 37° C. with 5% $CO_2$. SK-N-MC cells were maintained in Minimum Essential Medium (MEM) with Earle's salts, with L-glutamine (Gibco) and supplemented with 10% heat inactivated defined fetal bovine serum (HyClone), penicillin-streptomycin (Gibco) to a final concentration of 10 units penicillin and 10 µg streptomycin per ml and an additional 2 mM L-glutamine (Gibco). For the viability assays, cells were plated in 96-well plates in 100 µl of medium. SK-N-MC cells were seeded at an initial density of 20000 cells per well.

Doxorubicin and B12-Doxorubicin (stable) stocks and stock solutions, prepared in 5% DMSO in water, were stored at −20° C. and protected from light. Each compound was tested at six final concentrations covering ten-fold dilutions from 100 µM down to 10 nM. 10× stock solutions were made and 10 µl added to each of three wells containing cells. The viability assay and subsequent calculation were performed as described in EXAMPLE 4.

EXAMPLE 10

The following procedure was used to investigate the maximum tolerated dose of the vitamin B12-doxorubicin conjugate in Charles River nude (athymic) mice. Five groups of 5 mice each were weighed and then administered the first of 5 consecutive daily doses of intravenous conjugate; dose levels were 8, 16, 32, 48 and 54 mg/kg/day. Overall toxicity was assessed by weighing the mice twice weekly starting on Day 1 of dosing (the initial dose) and by frequent inspection for clinical signs and symptoms. The NCI definition of the MTD for cancer chemotherapy in mice was adopted for this study. The desirable MTD is that dose of drug mediating a maximum mean body weight loss of $\leq 10\%$ and no toxic deaths. The upper limit of the MTD is that dose causing a mean 20% weight loss in the group, and one death per 10 animals. After dosing once a day for 5 consecutive days, animals were monitored for another 5 days to address recurrent and latent toxicities.

EXAMPLE 11

The following procedure was used to investigate the tumor growth delay effects of the conjugate, particularly for the treatment of MX-1 human breast carcinoma xenograft in athymic mice using a two-cycle dosing regimen. Female nude Harlan mice are implanted subcutaneously with 1 $mm^3$ MX 1 solid tumor fragments in the flank. During the pre-dose phase of implantation and growth, tumors are initially monitored twice weekly, and then daily as the neoplasms approach the desired size of 80-120 mg. When the majority of tumors reached the targeted weight range (80-120 mg), mice are pair-matched into 5 treatment groups of 10 mice each. For purposes of this illustration on the effect of 2-cycles of treatment, data from 3 groups are shown: no treatment, 3 mg/kg/day (days 1-5, 21-25) intravenous Doxorubicin and 24 mg/kg/day (days 1-5, 21-25) intravenous bioconjugate. Test article administration began on this day, referred to as Day 1. The tumor growth delay endpoint is reached when the tumor on the mouse reaches 1.5 gm weight estimated by the formula: Tumor weight (mg)=$w^2 \times l/2 \times 1$ mg/mm$^3$, where w=width (mm) and l=length (mm) of the tumor. The median time to endpoint is calculated for each treatment group.

EXAMPLE 12

The following procedure was used to investigate body weight loss and recovery associated with doxorubicin treatment in tumor-bearing mice. This analysis was part of the efficacy studies specified in examples 3 and 11. The NCI definition of MTD for cancer chemotherapy in mice is used as guidelines to assess severity of morbidity in the animals. The upper limit of acceptability is 20% weight loss. Animals were weighed at the same time as their tumors were measured.

EXAMPLE 13

The following procedure was used to prepare the exemplary taxol-VB conjugate of FIG. 4b.

Fmoc-Phe-Lys(MMT)-PABC-2'-Taxol (14)

To a stirred solution of Fmoc-Phe-Lys(MMT)-PABC-PNP (0.0382 g, 36.10 μmol, 1.01 eq) and paclitaxel (Molecular Biosciences, 0.0305 g, 35.72 μmol, 1.0 eq) in methylene chloride (1 mL) was added DMAP (0.0053 g, 43.38 μmol, 1.21 eq). The yellow solution was stirred in the dark (wrapped with aluminum foil) at RT overnight. The reaction mixture was diluted with methylene chloride (50 ml), washed with water (25 ml×3), dried over MgSO$_4$. After removal of solvent, the residue was purified by silica column (2.4×10 cm), eluting with 2.5-5% methanol in methylene chloride, giving 0.04 g (63.2%) of pale yellow solid (14). ES(+)-MS: 1773.6(M+H), 1795.8(M+Na).

Phe-Lys(MMT)-PABC-2'-Taxol (15)

To a stirred solution of Fmoc-Phe-Lys(MMT)-PABC-2'-Taxol (40 mg) in dry THF (2 ml) was added 1,8-diazabicyclo[5.4.0]undec-7-ene (DBU, 20 μL). The solution was stirred at RT for 5 minutes. The reaction mixture was diluted with ether (18 mL). The resulting precipitate was collected, washed with ether (2 mL×3), dried in vacuo, giving 0.017 g (48.6%) of pale yellow solid (15). ES(+)-MS: 1550.9(M+H).

$B_{12}$-5'-OCONH(CH$_2$)$_5$CO-Phe-Lys(MMT)-PABC-2'-Taxol (16)

A solution of compound 15 (0.017 g, 0.10.96 μmol, 1.0 eq) and compound 11 (0.0186 g, 11.56 μmmol, 1.05 eq) in DMSO (1 mL) was stirred at room temperature for 3 hrs. HPLC showed a new peak at 22.9 min (Tr=7.6 min for SM, 20 to 100% B over 20 min; A: 0.1% HOAc/water; B: acetonitrile). The reaction mixture was added to 50 mL of stirred ether/CH$_2$Cl$_2$ (1:1), the resulting precipitate was collected, washed with acetone (2 ml×2), methylene chloride/ether (2 ml×3), dried in vacuo. 0.0165 g of red powder (16) was obtained.

$B_{12}$-5'-OCONH(CH$_2$)$_5$CO-Phe-Lys-PABC-2'-Taxol (17)

To a stirred suspension of compound 16 (0.0165 g, 5.418 μmol, 1.0 eq) in methanol (2 ml), water (2 ml) and methylene chloride (2 ml), was added anisole (0.15 ml, 1.3732 mmol, 253.4 eq) and dichloroacetic acid (0.3 ml, 3.6523 mmol, 674.1 eq). The solid dissolved and the mixture was stirred at RT for 1 hr. HPLC indicated most of the starting material consumed (Tr=16.6 min for product, 20 to 100% B over 20 min; A: 0.1% HOAc/water; B: acetonitrile). The reaction mixture was diluted with 0.1% acetic acid in water (100 mL), extracted with ether (100 mL×1, 50 mL×2), de-ethered by rotary evaporator, and concentrated by Waters Sep-Pak tC18 cartridge (P/N: WAT036810). The crude product was purified by HPLC:

Column: Waters Delta-Pak C18 15 um (P/N: WAT038506) 25×100 mm.

Flow rate: 13.7 mL/min.

Solvents: 0.1% HOAc/water (A) and acetonitrile (B).

Gradient: 0-4 min, 35% B isocratic; 4-24 min, 35-55% B.

The crude sample was dissolved in 35% methanol/0.1% HOAc/water (2 mL), filtered through 0.45 um Nylon syringe filter and loaded onto the column. Fractions having a retention time between around 10.0 min and 12.6 min were collected.

The fractions were then concentrated with a Waters Sep-Pak tC18 cartridge (P/N: WAT036810). The product was lyophilized to yield 2.2 mg of red powder.

The above in vitro and in vivo assays can be used to initially evaluate the activity of a conjugate as an anti-tumor agent and to compare the activity of a drug conjugate versus that of its corresponding free drug. Upon determination of a correlation between the two, a proper initial dosing regimen for the conjugate in a human subject may be determined.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

We claim:

1. An anti-tumor drug and cobalamin conjugate comprising:
   a. cobalamin, or a derivative or analogue thereof;
   b. a linker covalently bound to the 5'-OH moiety of cobalamin or cobalamin derivative; and
   c. an anti-tumor drug covalently bound to the linker thereby forming the conjugate wherein the drug is cleavable from the linker and/or the linker is cleavable from the drug by an intracellular enzyme; the conjugate is adapted for transport across a cellular membrane after complexation with transcobalamin; the drug is cleavable from the linker and/or the linker is cleavable from the drug by an intracellular enzyme; and the conjugate optionally possesses one or more protecting groups.

2. The anti-tumor drug and cobalamin conjugate of claim 1, wherein cobalamin is selected from the group consisting of vitamin B12, cyanocobalamin, aquocobalamin, hydroxycobalamin, methylcobalamin, adenosylcobalamin, cyanocobalamin carbanalide, desdimethyl cobalamin, monoethylamide cobalamin, methlyamide cobalamin, coenzyme B12, 5'-deoxyadenosylcobalamin, cobamamide derivatives, chlorocobalamin, sulfitocobalamin, nitrocobalamin, thiocyanatocobalamin, benzimidazole derivatives such as 5,6-dichlorobenzimidazole, 5-hydroxybenzimidazole, trimethylbenzimidazole, as well as adenosylcyanocobalamin ((Ade)CN-Gbl), cobalamin lactone, cobalamin lactam and the anilide, ethylamide, monocarboxylic, dicarboxylic and tricarboxylic acid derivative of VB12, proprionamide derivatives of VB12, 5-o-methylbenzylcobalmin, and analogues thereof wherein the cobalt is replaced by another metal.

3. The anti-tumor drug and cobalamin conjugate of claim 1, wherein the anti-tumor drug is selected from the group consisting of doxorubicin and taxol.

4. The anti-tumor drug and cobalamin conjugate of claim 1, wherein the linker is cleavable by way of an intracellular enzyme selected from the group of enzyme classes consisting of cathepsin, endo enzyme, glycosidase, metalloprotease, ribozyme, protease, esterase, and amidase.

5. The anti-tumor drug and cobalamin conjugate of claim 1, wherein the conjugate possesses reduced systemic toxicity as compared to the corresponding free anti-tumor drug.

6. A method of treating a tumor related disorder or disease comprising the step of administering to a subject in need thereof a therapeutically effective amount of conjugate according to claim 1.

7. An anti-tumor drug and cobalamin conjugate of the formula I:

$$\text{VB-(SPa)}_n\text{-CL-(SPb)}_m\text{-DG} \qquad \text{Formula I}$$

wherein,
 a. CL is a linker that is cleavable from the VB, SPa, SPb and/or DG by way of intracellular enzyme;
 b. VB is cobalamin, or a derivative or analogue thereof, covalently bound to CL and SPa, if present, via the 5'-OH group of the ribose ring of VB;
 c. SPa and SPb are optional spacers independently selected at each occurrence from the group consisting of a covalent bond, divalent functional group, or non-peptide residue, wherein SPa and SPb can be located on either side of CL; and
 d. DG is an anti-tumor drug possessing one or more functional groups by way which it is covalently bound to a spacer or CL; wherein n and m are independently selected at each occurrence from 0, 1, or 2; and the conjugate optionally possesses one or more protecting groups.

8. The anti-tumor drug and cobalamin conjugate of claim 7, wherein the divalent functional group is selected from the group consisting of —NHNH—, —NH—, —O—, —S—, —SS—, —CH$_2$—, —NHCO—, —CONH—, —CONHNHCO—, —N=N—, —N=CH—, —NHCH$_2$—, —NHN=CH—, —NHNHCH$_2$—, —SCH$_2$—, —CH$_2$S—, —NHC=ONH—, —NHC=SNH—, —NHC=NHNH—, —COO—, and —OCO—.

9. The anti-tumor drug and cobalamin conjugate of claim 7, wherein cobalamin is selected from the group consisting of vitamin B12, cyanocobalamin, aquocobalamin, hydroxycobalamin, methylcobalamin, adenosylcobalamin, cyanocobalamin carbanalide, desdimethyl cobalamin, monoethylamide cobalamin, methylamide cobalamin, coenzyme B12, 5'-deoxyadenosylcobalamin, cobamamide derivatives, chlorocobalamin, sulfitocobalamin, nitrocobalamin, thiocyanatocobalamin, benzimidazole derivatives, 5,6-dichlorobenzimidazole, 5-hydroxybenzimidazole, trimethylbanzimidazole, adenosylcyanocobalamin ((Ade)CN-Cbl), cobalamin lactone, cobalamin lactam and the anilide, ethylamide, monocarboxylic, dicarboxylic and tricarboxylic acid derivatives of VB12, proprionamide derivatives of VB12, 5-o-methylbenzylcobalmin, and analogues thereof wherein the cobalt is replaced by another metal.

10. the anti-tumor drug and cobalamin conjugate of claim 7, wherein n and m are independently selected from 1, 2 or 3.

11. The anti-tumor drug and cobalamin conjugate of claim 7, wherein the non-peptide residue is selected from the group consisting of —NH—C$_6$H$_4$—CH$_2$—O— and —NH(CH$_2$)$_5$C(=O)—.

12. The anti-tumor drug and cobalamin conjugate of claim 7, wherein the anti-tumor drug is selected from the group consisting of doxorubicin and taxol.

13. The anti-tumor drug and cobalamin conjugate of claim 7 having the one of the following formulas:
 a. VB-(SPa)$_p$-CL-DG (Formula II);
 b. VB-CL.(SPb)$_q$-DG (Formula III);
 c. VB-CL-DG (Formula IV);
 d. VB-CL-(SPa)$_p$-(SPb)$_q$-DG (Formula V);
 e. VB-(SPa)$_p$-(SPb)$_q$-CL-DG (Formula VI);
 f. VB-(SPa)$^2$(SPa)$^1$-CL-(SPb)$^2$-DG (Formula VII);
wherein p and q are independently selected from 1, 2 and 3.

14. The anti-tumor drug and cobalamin conjugate of claim 13 wherein:
 a. (SPa)$^1$ and (SPb)$^1$ are each independently selected at each occurrence from a divalent functional group and a covalent bond; and
 b. (SPa)$^2$ and (SPb)$^2$ are each independently selected at each occurrence from a non-peptide residue.

15. The anti-tumor drug and cobalamin conjugate of claim 14, wherein:
 a. (SPa)$^2$ and (SPb)$^2$ area each a divalent carbonyl; and
 b. (SPa)$^2$ and (SPb)$^1$ are each an —NH—, —S—, and/or —O— containing non-peptide residue.

16. The anti-tumor drug and cobalamin conjugate of claim 7, wherein the linker is cleavable by way of an intracellular enzyme selected from the group of enzyme classes consisting of cathepsin, endo enzyme, glycosidase, metalloprotease, ribozyme, protease, esterase, and amidase.

17. The anti-tumor drug and cobalamin conjugate of claim 7, wherein the conjugate possesses reduced systemic toxicity as compared to the corresponding free anti-tumor drug.

18. The anti-tumor drug and cobalamin conjugate of claim 17, wherein the conjugate possesses improved efficacy on a molar basis than the corresponding free anti-tumor drug.

19. the anti-tumor drug and cobalamin conjugate of claim 7, wherein the one or more functional groups are selected from the group consisting of a primary or secondary amine, hydroxyl, sulfhydryl, carboxyl, hydrazide, nitrile, aldehyde, and ketone.

20. The anti-tumor drug and cobalamin conjugate of claim 7, wherein the one or more functional groups comprises a derivatizable site on DG.

21. A method of treating a tumor related disorder or disease comprising the step of administering to a subject in need thereof a therapeutically effective amount of a conjugate according to claim 7.

* * * * *